United States Patent
Hwang et al.

(10) Patent No.: US 10,507,224 B2
(45) Date of Patent: Dec. 17, 2019

(54) COMPOSITION INCLUDING KIRENOL OR SIEGESBECKIA HERBA EXTRACT FOR MUSCLE FUNCTION IMPROVEMENT OR EXERCISE ABILITY ENHANCEMENT

(71) Applicant: AAT Costech Co., Ltd., Seoul (KR)

(72) Inventors: Jae-Kwan Hwang, Goyang-si (KR); Mi-Bo Kim, Seoul (KR); Chang Hee Kim, Seoul (KR)

(73) Assignee: AAT Costech Co., Ltd., Seoul (KR)

( * ) Notice: Subject to any disclaimer, the term of this patent is extended or adjusted under 35 U.S.C. 154(b) by 0 days.

(21) Appl. No.: 15/390,800

(22) Filed: Dec. 27, 2016

(65) Prior Publication Data

US 2017/0182106 A1    Jun. 29, 2017

Related U.S. Application Data

(63) Continuation of application No. PCT/KR2015/006655, filed on Jun. 29, 2015.

(30) Foreign Application Priority Data

| Jun. 27, 2014 | (KR) | 10-2014-0079536 |
| Jun. 27, 2014 | (KR) | 10-2014-0079538 |
| Jun. 29, 2015 | (KR) | 10-2015-0092315 |
| Jun. 29, 2015 | (KR) | 10-2015-0092336 |

(51) Int. Cl.
*A61K 36/28* (2006.01)
*A61K 31/047* (2006.01)

(52) U.S. Cl.
CPC ............ *A61K 36/28* (2013.01); *A61K 31/047* (2013.01); *A61K 2236/00* (2013.01)

(58) Field of Classification Search
None
See application file for complete search history.

(56) References Cited

U.S. PATENT DOCUMENTS

2008/0233216 A1* 9/2008 Park

FOREIGN PATENT DOCUMENTS

| CN | 101597212 | 12/2009 |
| KR | 10-2007-0076613 | 7/2007 |
| KR | 10-2013-0076465 | 7/2013 |
| WO | WO 2015/199516 | 12/2015 |

OTHER PUBLICATIONS

Lasich, C., "Muscle Weakness Linked to Arthritis", 2012, downloaded from "www.healthcentral.com/article/muscle-weakness-linked-to-arthritis", 2 pages.*
Huang et al., "Advances in the extraction of natural ingredients by high pressure extraction technology", Trends in Food Science & Technology, vol. 33, 2013, pp. 54-62.*
International Search report dated Sep. 24, 2015 From the Korean Intellectual Property Office Re. Application No. PCT/KR2015/006655 and Its Translation Into English. (6 Pages).
Korean Traditional Knowledge Portal "Siegesbeckia Glabrescens Makino", Korean Traditional Knowledge Portal, 5 P., Dec. 6, 2007.
Nugroho et al. "Quantitative Analysis of Kirenol in Siegesbeckia Glabrescens and S. Pubescens by HPLC-UV", Korean Journal of Pharmacognosy, 43(4): 286-290, 2012. Abstract, Introduction, Results and Discussion.
Notification of Reasons for Refusal dated Oct. 10, 2017 From the Japan Patent Office Re. Application No. 2017-520846 and Its Translation Into English. (11 Pages).
Korean Traditional Knowledge Portal "Siegesbeckia Glabrescens Makino", Korean Traditional Knowledge Portal, 3 pages, 2007.
Wang et al. "Topical Anti-Inflammatory and Analgesic Activity of Kirenol Isolated From Siegesbeckia Orientalis", Journal of Ethnopharmacology, 137(3): 1089-1094, Available Online Jul. 21, 2011.
Xiong et al. "Diterpenoids From Siegesbeckia Pubescens", Phytochemistry, 31(3): 917-921, Mar. 1992.

* cited by examiner

*Primary Examiner* — Savitha M Rao
*Assistant Examiner* — Gregg Polansky

(57) ABSTRACT

The present invention relates to a composition for muscle function improvement or exercise ability enhancement, the composition including kirenol, a *Siegesbeckia herba* extract, or a fraction of the *Siegesbeckia herba* extract as an active ingredient. Kirenol, the *Siegesbeckia herba* extract containing kirenol, or the *Siegesbeckia herba* extract fraction according to the present invention has an excellent effect of increasing muscle mass by increasing the protein expression of p-mTOR, which is a major gene concerned with muscle functions. Also, kirenol, the *Siegesbeckia herba* extract containing kirenol, or the *Siegesbeckia herba* extract fraction according to the present invention has an effect of remarkably enhancing exercise ability by increasing the protein expression of PGC-1α, which is a major gene concerned with exercise ability. In addition, the present invention is a natural product, and thus is safe for use without side effects and can be used as a medicine or food.

6 Claims, 10 Drawing Sheets

Specification includes a Sequence Listing.

FIG. 13 (a)
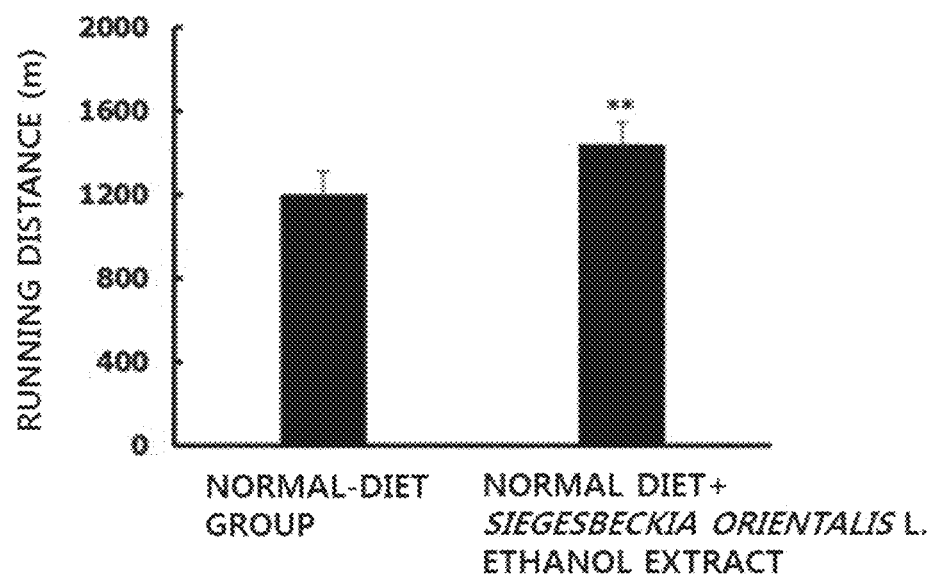
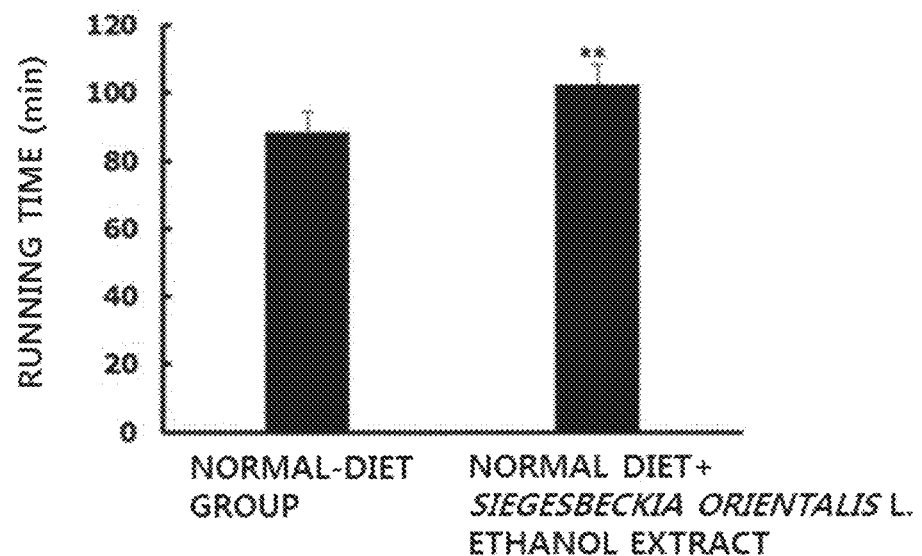
FIG. 13 (b)

FIG. 14 (a)
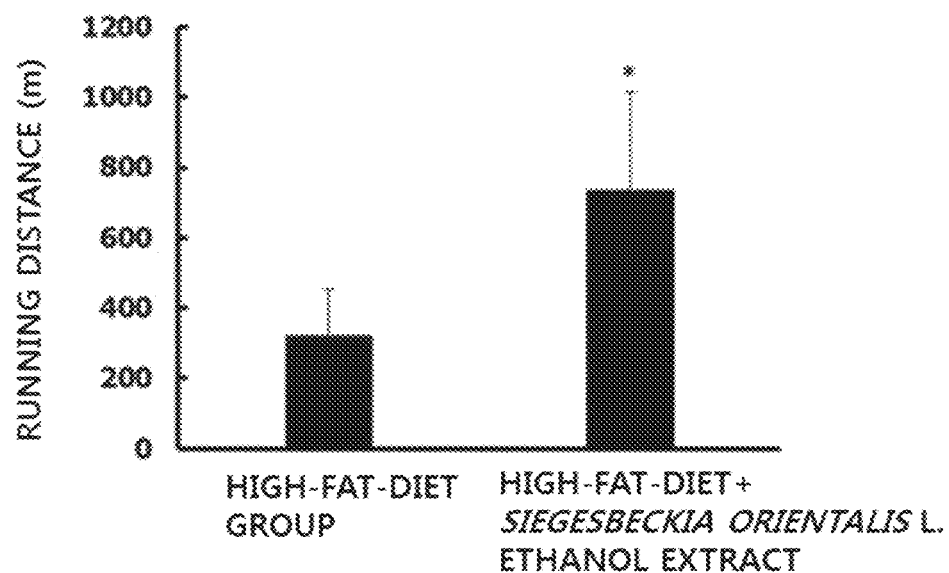
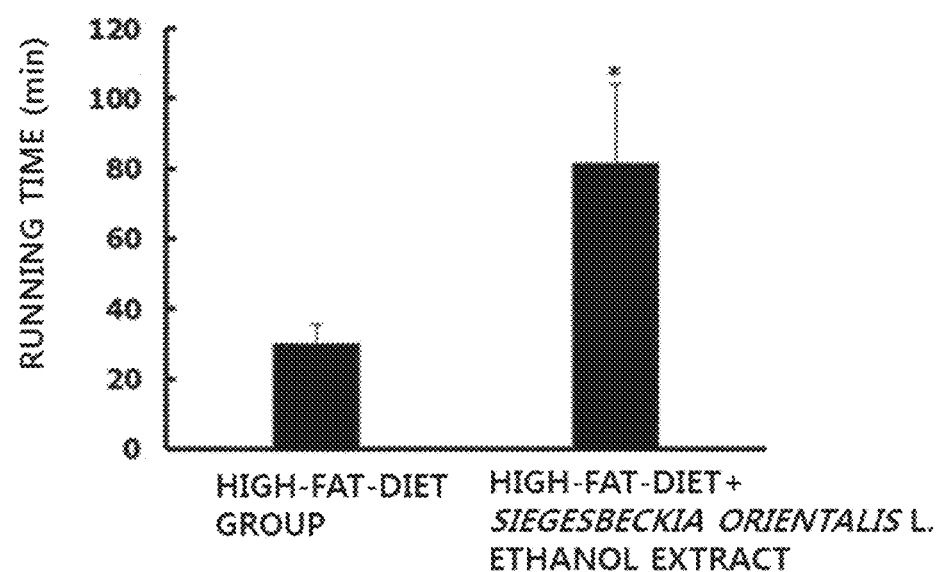
FIG. 14 (b)

COMPOSITION INCLUDING KIRENOL OR SIEGESBECKIA HERBA EXTRACT FOR MUSCLE FUNCTION IMPROVEMENT OR EXERCISE ABILITY ENHANCEMENT

RELATED APPLICATIONS

This application is a Continuation of PCT Patent Application No. PCT/KR2015/006655 having International filing date of Jun. 29, 2015, which claims priority of Korean Patent Applications Nos. 10-2014-0079538 filed on Jun. 27, 2014, 10-2014-0079536 filed on Jun. 27, 2014, 10-2015-0092336 filed on Jun. 29, 2015, and 10-2015-0092315 filed on Jun. 29, 2015. The contents of the above application are all incorporated by reference as if fully set forth herein in their entirety.

SEQUENCE LISTING STATEMENT

The ASCII file, entitled 68635SequenceListing.txt, created on Dec. 25, 2016, comprising 4,672 bytes, submitted concurrently with the filing of this application is incorporated herein by reference.

FIELD AND BACKGROUND OF THE INVENTION

Field of the Invention

The present invention relates to a composition for muscle function improvement or exercise ability enhancement, the composition including kirenol, a *Siegesbeckia herba* extract, or a fraction of the *Siegesbeckia herba* extract as an active ingredient.

Discussion of Related Art

It has been known that the decline in human physical activity over the past 50 to 100 years is associated with a growing incidence of metabolic diseases such as type 2 diabetes, obesity, and cardiovascular diseases. Lack of physical activity is the fourth leading cause of death as reported by the World Health Organization. For this reason, organizations such as the World Health Organization, the American Heart Association, and the British Heart Foundation recommend a minimum of 30 minutes of aerobic exercise for at least five days a week. In fact, exercise reduces the incidence of diabetes, obesity, breast cancer, and colorectal cancer, and has a good therapeutic effect on depression (Br. J. Pharmacol. 170:1153-1166, 2013, Am. J. Cardiol. 110: 58B-68B, 2012).

One of the representative methods for improving exercise ability by promoting energy consumption is to increase fatty acid oxidation by mitochondria to produce adenosine triphosphate (ATP) energy. It has been discovered that the number and performance of the regulating mitochondria is controlled by a coactivator referred to as peroxisome proliferator-activated receptor-gamma coactivator 1 alpha (PGC-1α), and that PGC-1α activity is regulated by SIRT1 (sirtuin 1) (EMBO. J. 26: 1913-1923, 2007, Cell Metab. 1: 361-370, 2005).

Scarpulla and his co-workers identified proteins known as nuclear respiratory factors (NRFs) (J. Cell. Biochem. 97: 673-683, 2006). Proteins of the NRF family activate the replication and transcription in mitochondria by binding to promoters of various genes in the nucleus. It has been discovered that the production of mitochondria is induced by activated mitochondrial replication and transcription. Also, it has been found that the expression of proteins of the NRF family is enhanced as the proteins physically interact with PGC-1α (Cell 98:115-24, 1999).

In addition, AMPK, p-AMPK, PPARδ, ERRα, Tfam, and the like are known as factors associated with exercise ability enhancement.

Meanwhile, muscle atrophy refers to muscle weakness and muscle degeneration and is caused by a gradual decrease in muscle mass (Cell 119: 90710, 2004). Muscle atrophy is accelerated by lack of activity, oxidative stress, and chronic inflammation, and weakens muscle function and exercise ability (Clin. Nutr. 26: 524-534, 2007). Muscle mass is the most important determinant of muscle functions and is maintained by the balance between protein synthesis and protein degradation. Muscle atrophy occurs when protein degradation exceeds protein synthesis (Cell Biol. 37: 1985-1996, 2005).

Muscle size is regulated by intracellular signaling pathways that induce anabolism or catabolism within muscle. When signals inducing muscle protein synthesis exceed signals inducing muscle protein degradation, more muscle proteins are synthesized. An increase in muscle protein synthesis results in an increase in muscle size (hypertrophy) or an increase in the number of muscle fibers (hyperplasia) due to an increase in the amount of muscle proteins (The Korea Journal of Sports Science 30: 1551-1561, 2011).

Factors inducing hypertrophy induce protein synthesis by phosphorylating downstream proteins upon the stimulation of phosphatidylinositol-3 kinase (PI3K)/Akt pathways in muscle cells. Among the factors, the activation of mechanistic target of rapamycin (mTOR) due to PI3K/Akt signaling is recognized as a main growth signaling mechanism that integrates various growth signals in cells. The activation of mTOR contributes to an increase in the muscle mass by inducing muscle protein synthesis through the activation of 4E-binding protein 1 (4E-BP1) and phosphorylated 70-kDa ribosomal S6 kinase (p70S6K), both of which are downstream targets (The Korea Journal of Sports Science 30: 1551-1561, 2011, J Biol Chem 278:40717-40722, 2003).

Muscle cell differentiation and muscle formation are regulated by various muscle regulatory factors (Cell Mol Life Sci 70: 4117-4130, 2013). Among the factors, MyoD initiates the expression of genes specific for muscle differentiation and induces mesenchymal stem cells to differentiate into myoblasts. Myogenin, which is regulated by MyoD, is the most important factor in the fusion of myoblasts, and is involved with the formation of myotubes. The muscle fibers formed through the above process form a bundle and eventually form muscles (Cell Mol Life Sci 70: 4117-4130, 2013; Sci Signal 6: re2, 2013).

*Siegesbeckia herba* is the dried aerial part of *Siegesbeckia glabrescens* Mak., *Siegesbeckia pubescens* Mak., or *Siegesbeckia orientalis* L., all of which are *Siegesbeckia* spp. and members of the genus *Siegesbeckia* and the family Asteraceae. *Siegesbeckia glabrescens* Mak., also known as Jindeukchal in Korea, is reported to exhibit antimicrobial (Int. J. Food Microbiol. 160: 260-266, 2013), anticancer (Oncol. Rep. 30: 221-226, 2013), antidiabetic (J. Enzyme Inhib. Med. Chem. 21: 379-383, 2006), anti-inflammatory (Food Agric. Immunol. 22: 145-160, 2011) activities, and the like. *Siegesbeckia pubescens* Mak., also known as Teoljindeukchal in Korea, is reported to exhibit anti-inflammatory and analgesic (Pak. J. Pharm. Sci. 21: 89-91, 2008), antioxidant and anti-obesity (Kor. J. Microbiol. Biotechnol. 41: 341-349, 2013), wound healing (J. Ethnopharmacol. 134: 1033-1038, 2011), arthritis treatment (Phytomedicine 19: 882-889, 2012) activities, and the like. *Siegesbeckia orientalis* L., also known as Jejujindeukchal in Korea, is reported to exhibit anticancer (Natural Product Radiance 6: 34-39, 2007), anti-inflammatory (Chem. Biodivers. 3: 754-761, 2006), antioxidant (Korean J. Pharmacogn. 36: 150-163, 2005) activities, and the like.

Kirenol is a diterpenoid mainly found in *Siegesbeckia herba* and is reported to exhibit anti-inflammatory and analgesic effects (J. Ethnopharmacol. 137: 1089-1094, 2011), an antimicrobial effect (Pharmacogn. Mag. 8: 149-155, 2012), an arthritis treatment effect (Phytomedicine 19: 882-889, 2012), an anti-obesity effect (BBRC 445, 433-438, 2014), and the like.

However, prior to the present invention, there has been no report on the effect of *Siegesbeckia herba* or kirenol in terms of muscle function improvement or exercise ability enhancement.

SUMMARY OF THE INVENTION

Hence, the present inventors have searched for a natural substance that exhibits an excellent muscle-function modulating activity or an excellent exercise-ability enhancement activity and is safe for use. As a result, the present inventors confirmed that kirenol, a *Siegesbeckia herba* extract containing kirenol, or a fraction of the *Siegesbeckia herba* extract has a muscle function improvement activity and an exercise-ability enhancement activity, and thus completed the present invention.

Therefore, the present invention is directed to providing a composition including a *Siegesbeckia herba* extract as an active ingredient for muscle function improvement or exercise ability enhancement.

Also, the present invention is directed to providing a composition including a compound of the following Structural Formula 1 as an active ingredient for muscle function improvement or exercise ability enhancement:

[Structural Formula 1]

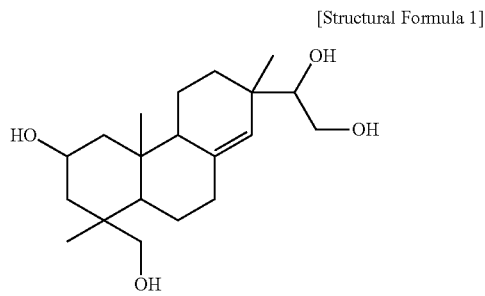 [SMILES: CC1(C(O)CO)C=C2CCC3C(C)(CO)CC(O)CC3(C)C2CC1]

In order to solve the aforementioned problems, the present invention provides a pharmaceutical composition and a food composition that includes a *Siegesbeckia herba* extract or a fraction of the *Siegesbeckia herba* extract as an active ingredient for muscle function improvement or exercise ability enhancement.

Also to solve the aforementioned problems, the present invention provides a pharmaceutical composition and a food composition that include a compound represented by the following Structural Formula 1 as an active ingredient for muscle function improvement or exercise ability enhancement:

[Structural Formula 1]

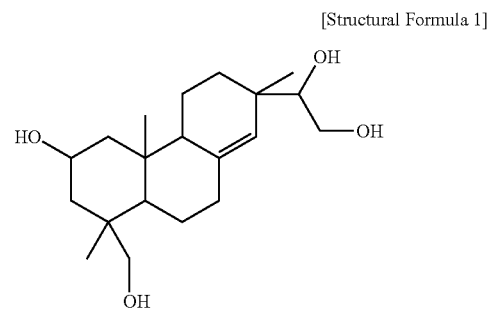 [SMILES: CC1(C(O)CO)C=C2CCC3C(C)(CO)CC(O)CC3(C)C2CC1]

Kirenol, the *Siegesbeckia herba* extract containing kirenol, or the *Siegesbeckia herba* extract fraction according to the present invention has an excellent effect of increasing muscle mass by increasing the protein expression of p-mTOR, which is a major gene concerned with muscle function improvement. Also, kirenol, the *Siegesbeckia herba* extract containing kirenol, or the *Siegesbeckia herba* extract fraction according to the present invention has an effect of remarkably enhancing exercise ability by increasing the protein expression of PGC- 1α, which is a major gene concerned with exercise ability.

In addition, the present invention is a natural product, and thus is safe for use without side effects and can be used as a medicine or food.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the accompanying drawings, in which:

FIGS. 13(a) and 13(b) show the measurement of changes in exercise ability in a normal-diet animal model after the administration of a kirenol-containing ethanol extract of *Siegesbeckia orientalis* L. (13(a): running distance, 13(b): running time);

FIGS. 14(a) and 14(b) show the measurement of changes in exercise ability in a high-fat-diet induced obese animal model after the administration of a kirenol-containing ethanol extract of *Siegesbeckia orientalis* L. (14(a): running distance, 14(b): running time);

DESCRIPTION OF SPECIFIC EMBODIMENTS OF THE INVENTION

Figure 1:
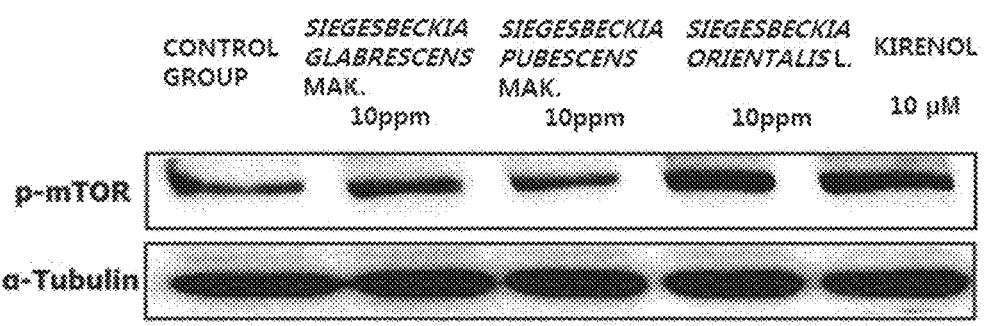
FIG. 1 shows the measurement of p-mTOR protein expression levels in L6 muscle cells after treatment with kirenol or a kirenol-containing ethanol extract of *Siegesbeckia glabrescens* Mak., *Siegesbeckia pubescens* Mak., or *Siegesbeckia orientalis* L.

Hereinafter, the configuration of the present invention will be described in detail.

The present invention provides an application of a *Siegesbeckia herba* extract, a fraction of the *Siegesbeckia herba* extract, or a compound represented by the following Structural Formula 1 for muscle function improvement or exercise ability enhancement; a composition including a *Siegesbeckia herba* extract, a fraction of the *Siegesbeckia herba* extract, or a compound represented by the following Structural Formula 1 for muscle function improvement or exercise ability enhancement; or a method of improving muscle function or enhancing exercise ability, the method including administering a *Siegesbeckia herba* extract, a fraction of the *Siegesbeckia herba* extract, or a compound represented by the following Structural Formula 1 to a subject.

[Structural Formula 1]

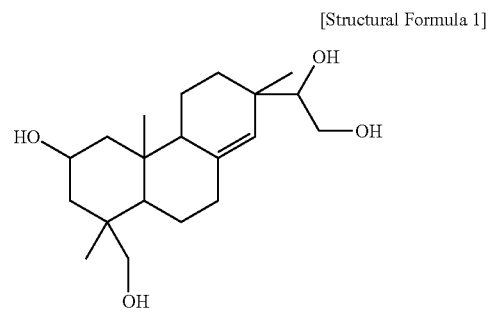 [SMILES: CC1(C(O)CO)C=C2CCC3C(C)(CO)CC(O)CC3(C)C2CC1]

In the present specification, "*Siegesbeckia herba*" refers to the dried aerial part of *Siegesbeckia glabrescens* Mak., *Siegesbeckia pubescens* Mak., or *Siegesbeckia orientalis* L., all of which are *Siegesbeckia* spp., members of the genus *Siegesbeckia* and the family Asteraceae. In Korea, *Siegesbeckia glabrescens* Mak., *Siegesbeckia pubescens* Mak., and *Siegesbeckia orientalis* L. are also known as Jindeukchal, Teoljindeukchal, and Jejujindeukchal, respectively.

In the present specification, "*Siegesbeckia herba* extract" and "*Siegesbeckia* spp. extract" are used interchangeably, and *Siegesbeckia herba* extract refers to an extract obtained from *Siegesbeckia herba*. As a method of preparing such a *Siegesbeckia herba* extract, any common extraction method known in the art may be used without limitation. For example, the *Siegesbeckia herba* extract may be obtained by extracting whole *Siegesbeckia* spp. or a part (leaves or roots) of *Siegesbeckia* spp. using one or more solvents selected from the group consisting of water, organic solvents having one to six carbon atoms, subcritical water, and supercritical fluids.

In the present specification, "fraction" refers to a resulting material obtained by fractionation, which is a method of separating a specific ingredient or a specific group from a mixture containing various constituent substances. Methods of preparing such a fraction are well known in the art, and any method known in the art may be used without limitation. For example, techniques such as solvent fractionation, silica gel chromatography, and prep-HPLC may be used to prepare a specific fraction enriched with active substances.

In one embodiment, a fraction of a *Siegesbeckia herba* extract may be obtained by fractionating the *Siegesbeckia herba* extract using ethyl acetate, methanol, or a solvent mixture of ethyl acetate and methanol.

In the present specification, "muscle" collectively refers to tendon, muscle, and sinew. Also, "muscle function" refers to the ability of muscle to exert a force through muscle contraction, and encompasses muscle strength, which is the ability of muscle to exert maximum retraction to overcome resistance; muscular endurance, which is the ability of muscle to repeat contraction and relaxation for a given weight and is measured in terms of the duration and number of repetitions; and explosive muscular strength, which is the ability to exert strong power in a short period of time. Such muscle functions are proportional to the muscle mass. The term "muscle function improvement" or "improvement of muscle functions" refers to the act of making muscle functions better.

In the present specification, "composition for muscle function improvement" or "composition for improving muscle functions" refers to a composition that includes a material effective for improving muscle functions as an active ingredient, and includes a pharmaceutical composition or a food composition within the scope thereof.

In the present specification, "exercise ability" refers to the ability to perform body movements seen in everyday life or sports quickly, strongly, accurately, steadily, and skillfully, wherein such body movements are classified into running, jumping, throwing, swimming, and the like by appearance. Exercise ability is defined by factors such as muscle strength, agility, and endurance. The term "exercise ability enhancement" or "enhancement of exercise ability" refers to the act of increasing or improving exercise ability.

In the present specification, "composition for exercise ability enhancement" or "composition for enhancing exercise ability" refers to a composition that includes a material effective for enhancing exercise ability as an active ingredient, and includes a pharmaceutical composition or a food composition within the scope thereof.

In addition to a *Siegesbeckia herba* extract or a fraction of the *Siegesbeckia herba* extract, the composition for muscle function improvement or exercise ability enhancement according to the present invention may further include one or more types of active ingredients exhibiting functions that are the same as or similar to functions of the *Siegesbeckia herba* extract or the *Siegesbeckia herba* extract fraction. For example, an ingredient known in the art to be effective for muscle function improvement or exercise ability enhancement may be included in the composition. When such an additional ingredient is included in the composition of the present invention, a composition with further improved efficacy for improving muscle functions or enhancing exercise ability may be attained. When the addition of such an ingredient to the composition of the present invention is contemplated, dermal safety according to the use of multiple active ingredients, ease of formulation, and stability of active ingredients may be taken into consideration. In one embodiment of the present invention, the composition may additionally include one or more types of ingredients selected from the group consisting of a *Kaempferia parviflora* extract, a *Piper retrofractum* Vahl. fruit extract, myricetin, a cucurbitane extract, a *Boesenbergia pandurata* extract, a grape root extract, a *Phragmites rhizome* extract, and a red ginseng extract as an ingredient known in the art to be effective for muscle function improvement or exercise ability enhancement. Such an additional ingredient may be included in the composition at a concentration of 0.0001 wt % to 10 wt % with respect to the total weight of the composition. For example, a content of the additional ingredient in the composition may be 0.0001 wt % to 1 wt %, 0.0001 wt % to 0.1 wt %, 0.0001 wt % to 0.001 wt %, 0.001 wt % to 10 wt %, 0.001 wt % to 1 wt %, 0.001 wt % to 0.1 wt %, 0.01 wt % to 10 wt %, or 0.01 wt % to 1 wt %, and the range of the content may be adjusted according to requirements such as ease of formulation of the compound of the above Structural Formula 1 and dermal safety.

The composition including a *Siegesbeckia herba* extract or a fraction of the *Siegesbeckia herba* extract as an active ingredient for muscle function improvement or exercise ability enhancement according to the present invention may be a pharmaceutical composition or a food composition.

The composition including the compound represented by Structural Formula 1 as an active ingredient for muscle function improvement or exercise ability enhancement according to the present invention may be a pharmaceutical composition or a food composition:

[Structural Formula 1]

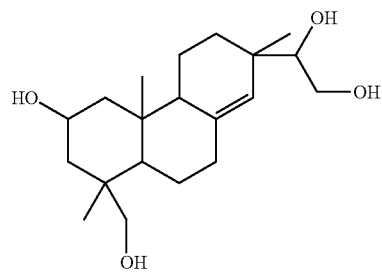

The compound of the above Structural Formula 1 may be any possible isomer. For example, the compound of Structural Formula 1 may be a compound represented by the following Structural Formula 2.

[Structural Formula 2]

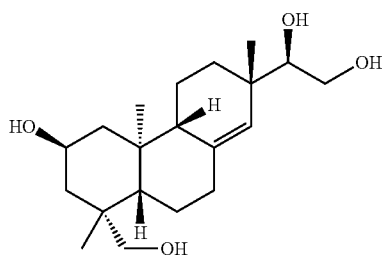

The compound of the above Structural Formula 2 is known as kirenol.

The compound of Structural Formula 1 or the compound of Structural Formula 2 may have been separated from a plant extract or synthesized for use. Alternatively, a commercially available compound may be purchased for use.

In one embodiment, the above compound represented by Structural Formula 1 or the compound represented by Structural Formula 2 may have been separated from a *Siegesbeckia herba* extract.

In one embodiment, the *Siegesbeckia herba* extract may be a plant extract obtained from one or more selected from the group consisting of *Siegesbeckia glabrescens* Mak., *Siegesbeckia pubescens* Mak., and *Siegesbeckia orientalis* L. For example, the *Siegesbeckia herba* extract may be an ethanol extract, a hot water extract, a hexane extract, an ethyl acetate extract, or an ultra-high pressure extract obtained from dried leaves and stems of *Siegesbeckia glabrescens* Mak., *Siegesbeckia pubescens* Mak., or *Siegesbeckia orientalis* L.

In one embodiment, the *Siegesbeckia herba* extract may be obtained by extracting *Siegesbeckia herba* using one or more solvents selected from the group consisting of water, organic solvents having one to six carbon atoms, subcritical water, and supercritical fluids. For example, the *Siegesbeckia herba* extract may be obtained by extracting *Siegesbeckia* spp. under ultra-high pressure conditions of 100 MPa or more. If necessary, the *Siegesbeckia herba* extract may be prepared by additionally performing filtration and concentration according to a method known in the art.

In one embodiment, the organic solvent having one to six carbon atoms may be one or more selected from the group consisting of alcohols, acetone, ethers, benzene, chloroform, ethyl acetate, methylene chloride, hexane, cyclohexane, and petroleum ethers, all of which have one to six carbon atoms.

In addition, the *Siegesbeckia herba* extract of the present invention may be obtained through the extraction of dried *Siegesbeckia herba* using purified water, ethanol, subcritical water, or supercritical carbon dioxide, all of which are suitable for food processing, and subsequent purification. Alternatively, the *Siegesbeckia herba* extract may be obtained by extracting dried *Siegesbeckia herba* with an ultra-high pressure extraction device and then purifying the extracted substances, or by separating *Siegesbeckia* spp. from an oil obtained through direct compression and then purifying the separated substances. For example, the *Siegesbeckia herba* extract may be obtained by extracting *Siegesbeckia herba* under ultra-high pressure conditions of 100 MPa or more.

In one embodiment, the *Siegesbeckia herba* extract fraction may be obtained by fractionating the *Siegesbeckia herba* extract using ethyl acetate, methanol, or a solvent mixture of ethyl acetate and methanol.

When the composition of the present invention is a pharmaceutical composition, the composition may be used for improving muscle functions by preventing or treating a muscle disease induced by muscle wasting or muscle degeneration. Muscle wasting and muscle degeneration are caused by genetic factors, acquired factors, aging, or the like, and muscle wasting is characterized by the gradual loss of muscle mass and the weakening and degeneration of muscles, especially skeletal or voluntary muscle and cardiac muscle. Examples of related diseases include atony, muscle atrophy, muscular dystrophy, muscle degeneration, myasthenia, and sarcopenia. The composition of the present invention is effective for increasing muscle mass, and types of muscles affected by the composition are not limited.

The pharmaceutical composition of the present invention may include kirenol, a *Siegesbeckia herba* extract containing kirenol, or a pharmaceutically acceptable salt of a fraction of the *Siegesbeckia herba* extract. In the present specification, the term "pharmaceutically acceptable" refers to being physiologically acceptable and typically not causing an allergic reaction or a similar reaction when administered to a human. Preferably, the pharmaceutically acceptable salt is an acid addition salt formed using a pharmaceutically acceptable free acid.

The aforementioned kirenol, *Siegesbeckia herba* extract containing kirenol, or pharmaceutically acceptable salt of a fraction of the *Siegesbeckia herba* extract may be an acid addition salt formed using an organic acid or an inorganic acid. Examples of the organic acid include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzene sulfonic acid, p-toluenesulfonic acid, and methanesulfonic acid. Examples of the inorganic acid include hydrochloric acid, bromic acid, sulfuric acid, phosphoric acid, nitric acid, carbonic acid, and boric acid. The acid addition salt is preferably in the form of a hydrochloride or an acetate, and is more preferably in the form of a hydrochloride.

The aforementioned acid addition salt is prepared according to a common method of preparing a salt, such as: a) directly mixing an acid with kirenol, a *Siegesbeckia herba* extract containing kirenol, or a fraction of the *Siegesbeckia herba* extract; b) dissolving one of kirenol, the *Siegesbeckia herba* extract containing kirenol, or the *Siegesbeckia herba* extract fraction into a solvent or a water-containing solvent and then performing mixing; or c) adding kirenol, the *Siegesbeckia herba* extract containing kirenol, or the *Siegesbeckia herba* extract fraction into an acid in a solvent or a hydrated solvent and then performing mixing.

In addition to the above, examples of the possible salts further include GABA salts, gabapentin salts, pregabalin salts, nicotinates, adipates, hemimalonates, cysteine salts, acetylcysteine salts, methionine salts, arginine salts, lysine salts, ornithine salts, and aspartates.

In addition, the pharmaceutical composition of the present invention may further include a pharmaceutically acceptable carrier.

For example, the pharmaceutically acceptable carrier may be a carrier for oral administration or a carrier for parenteral administration. The carrier for oral administration may be lactose, starch, a cellulose derivative, magnesium stearate, stearic acid, or the like. Also, the carrier for parenteral administration may be water, suitable oil, saline, aqueous glucose, a glycol, or the like. In addition, a stabilizer or a preservative may also be used as the pharmaceutically acceptable carrier. Suitable stabilizers include antioxidants such as sodium hydrogen sulfite, sodium sulfite, and ascorbic acid. Suitable preservatives include benzalkonium chloride, methylparaben, propylparaben, and chlorobutanol. Other pharmaceutically acceptable carriers may be found among those listed in the following document: Remington's Pharmaceutical Sciences, 19th ed., Mack Publishing Company, Easton, Pa., 1995.

The pharmaceutical composition of the present invention may be administered to mammals, including humans, by any method. For example, the pharmaceutical composition may be administered orally or parenterally. Parenteral administration methods include, but are not limited to, intravenous administration, intramuscular administration, intraarterial administration, intramedullary administration, intradural administration, intracardiac administration, transdermal administration, subcutaneous administration, intraperitoneal administration, intranasal administration, enteral administration, topical administration, sublingual administration, and rectal administration.

The pharmaceutical composition of the present invention may be formulated into a preparation for oral administration or a preparation for parenteral administration according to the route of administration as described above. The pharmaceutical composition may be formulated using one or more among buffers (e.g., saline or phosphate buffered saline), antioxidants, bacteriostatic agents, chelating agents (e.g., EDTA or glutathione), fillers, extenders, binders, adjuvants (e.g., aluminum hydroxide), suspending agents, thickeners, wetting agents, disintegrants, surfactants, diluents, and excipients.

Preparations for oral administration include tablets, pills, powders, granules, liquids, gels, syrups, slurries, suspensions, capsules, and the like. The preparations may be prepared by mixing the pharmaceutical composition of the present invention with at least one excipient such as starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethyl cellulose, hydroxypropyl methylcellulose, and gelatin. For example, tablets or sugarcoated tablets may be obtained by mixing an active ingredient with a solid excipient, milling the mixture, adding a suitable adjuvant thereinto, and then processing the resulting substances into a granule mixture.

In addition to simple excipients, lubricants such as magnesium stearate and talc are also used. In the case of a liquid preparation, various excipients such as wetting agents, sweetening agents, fragrances, and preservatives may be included in addition to water or liquid paraffin, both of which are commonly used simple diluents.

In some cases, crosslinked polyvinylpyrrolidone, agar, alginic acid, sodium alginate, or the like may be added as a disintegrant. Also, an anti-coagulant, a lubricant, a wetting agent, a flavoring agent, an emulsifying agent, an antiseptic agent, or the like may be additionally included.

For parenteral administration, the pharmaceutical composition of the present invention may be formulated, along with a suitable parenteral carrier, in the form of an injection, a percutaneous preparation, and a nasal inhaler according to a method known in the art. The injection should be sterilized and protected against contamination of microorganisms such as bacteria and fungi. Examples of a carrier suitable for the injection may include solvents or dispersion media such as water, ethanol, polyols (e.g., glycerol, propylene glycol, and liquid polyethylene glycol), mixtures thereof and/or vegetable oils, but are not limited thereto. More preferably, an isotonic solution such as Hank's solution, Ringer's solution, triethanolamine-containing phosphate buffered saline (PBS) or sterilized water for injection, 10% ethanol, 40% propylene glycol, and 5% dextrose is used as a suitable carrier. To protect the injection against contamination of microorganisms, a variety of antimicrobial agents and antifungal agents such as parabens, chlorobutanol, phenol, sorbic acid, and thimerosal may be additionally included. Also, in most cases, the injection may further include an isotonic agent such as sugar or sodium chloride.

When the pharmaceutical composition is prepared as a percutaneous preparation, the composition may take various forms such as an ointment, a cream, a lotion, a gel, a liquid for external use, a paste, a liniment, and an aerosol. In this case, "percutaneous administration" refers to administering a pharmaceutical composition locally to skin so that an effective amount of an active ingredient included in the pharmaceutical composition is delivered into skin.

In the case of an inhaler, the compound according to the present invention may be delivered in a convenient manner in the form of a pressurized pack or an aerosol spray from a nebulizer by using a suitable propellant such as dichlorofluoromethane, trichlorofluoromethane, dichlorotetrafluoroethane, and carbon dioxide or other suitable gases. In the case of a pressurized aerosol, the unit dosage may be determined by providing a valve that delivers a metered amount. For example, gelatin capsules and cartridges for use in an inhaler or an insufflator may be formulated to contain a powder mixture of a compound and a suitable powder base such as lactose and starch. Preparations for parenteral administration are listed in "Remington's Pharmaceutical Science, 15th Edition, 1975. Mack Publishing Company, Easton, Pa. 18042, Chapter 87: Blaug, Seymour", which is a prescription commonly known in pharmaceutical chemistry.

The pharmaceutical composition of the present invention may provide preferred effects of muscle function improvement or exercise ability enhancement when including an effective amount of kirenol, a *Siegesbeckia herba* extract, or a fraction of the *Siegesbeckia herba* extract. In the present specification, "effective amount" refers to an amount that results in better response than the response of a negative control, and preferably refers to an amount sufficient to improve muscle functions or enhance exercise ability. In the pharmaceutical composition of the present invention, kirenol or a *Siegesbeckia herba* extract containing kirenol may account for 0.01 to 99.99% of the composition, and a pharmaceutically acceptable carrier may account for the remainder. The effective amount of kirenol, a *Siegesbeckia herba* extract, or a fraction of the *Siegesbeckia herba* extract included in the pharmaceutical composition of the present invention may vary depending on a form that the composition takes for commercialization.

The total effective amount of the pharmaceutical composition of the present invention may be administered to a patient as a single dose or a multiple dose according to a long-term fractionated treatment protocol. A content of an active ingredient in the pharmaceutical composition of the present invention may be varied depending on the severity of a disease. The pharmaceutical composition may be administered as a single dose or a multiple dose so that preferably 0.01 to 50 mg and more preferably 0.1 to 30 mg of kirenol or the *Siegesbeckia herba* extract containing kirenol is provided per 1 kg body weight a day in the case of parenteral administration and preferably 0.01 to 100 mg and more preferably 0.01 to 10 mg of kirenol or the *Siegesbeckia herba* extract containing kirenol is provided per 1 kg body weight a day in the case of oral administration. However, since a content of kirenol or the *Siegesbeckia herba* extract containing kirenol is determined based on various factors such as the route of administration, the frequency of treatment, the age, weight, health, and sex of a patient, the severity of a disease, diet, and an excretion rate, a person of ordinary skill in the art may be able to determine a suitable effective dose of kirenol or the *Siegesbeckia herba* extract containing kirenol for use in muscle function improvement or exercise ability enhancement accordingly. The pharmaceutical composition of the present invention is not particularly limited to a specific formulation, route of administration, and administration method as long as intended effects of the present invention are attained.

The pharmaceutical composition of the present invention may be used either alone or along with a method that involves surgery, radiation therapy, hormone therapy, chemotherapy, or use of a biological response modifier.

Also, the pharmaceutical composition of the present invention may be provided as a preparation for external use that includes kirenol, a *Siegesbeckia herba* extract, or a fraction of the *Siegesbeckia herba* extract as an active ingredient.

When the pharmaceutical composition of the present invention is used for external use on skin, the composition may further include adjuvants commonly used in the field of dermatology. Examples of such adjuvants include fatty substances, organic solvents, solubilizers, thickeners, gelling agents, softening agents, antioxidants, suspending agents, foaming agents, fragrances, surfactants, water, ionic emulsifiers, nonionic emulsifiers, fillers, sequestering agents, chelating agents, preservatives, vitamins, blocking agents, wetting agents, essential oils, dyes, pigments, hydrophilic activators, lipophilic activators, and any other ingredient commonly used in preparations for external use on skin, e.g. lipid vesicles. In addition, the ingredients may be included in an amount commonly used in the field of dermatology.

When external use on skin is contemplated, the pharmaceutical composition of the present invention may be provided in the form of an ointment, a patch, a cream, or a spray, but is not limited thereto.

The composition of the present invention may also be a food composition. When the composition for muscle function improvement or exercise ability enhancement according to the present invention is a food composition, the composition may be used for preventing or treating a muscle disease induced by muscle wasting or muscle degeneration. Muscle wasting and muscle degeneration are caused by genetic factors, acquired factors, aging, or the like, and muscle wasting is characterized by the gradual loss of muscle mass and the weakening and degeneration of muscles, especially skeletal or voluntary muscle and cardiac muscle. Examples of related diseases include atony, muscle atrophy, muscular dystrophy, muscle degeneration, myasthenia, and sarcopenia. The composition of the present invention is effective for increasing muscle mass, and types of muscles affected by the composition are not limited.

The food composition of the present invention may comprise all types of forms such as functional foods, nutritional supplements, health foods, food additives, and animal foods, and is targeted at feeding animals including humans and livestock.

Such a food composition may be prepared into various forms according to a common method known in the art. The general food may be prepared by adding kirenol or a kirenol-containing *Siegesbeckia herba* extract into beverages (including alcoholic beverages), fruits and processed foods thereof (e.g., canned fruit, bottled fruit, jam, and marmalade), fish and processed foods thereof, meat and processed foods thereof (e.g., ham and corn beef sausage), breads and noodles (e.g., udon, buckwheat noodles, ramen, spaghetti, and macaroni), juices, various drinks, cookies, taffies, dairy products (e.g., butter and cheese), edible vegetable oils, margarine, vegetable proteins, retort foods, frozen foods, various seasonings (e.g. soybean paste, soy sauce, and sauces), or the like, but preparation methods thereof are not limited to those listed above. Also, a nutritional supplemental food may be prepared by adding kirenol or the kirenol-containing *Siegesbeckia herba* extract into capsules, tablets, pills, or the like, but preparation methods thereof are not limited to those listed above. Moreover, the food composition in the form of a health food or a health functional food may be prepared, for example, by processing kirenol or the kirenol-containing *Siegesbeckia herba* extract itself in the form of tea, a juice, or a drink and then liquefying, granulating, encapsulating, or powdering the same into a drinkable form (a health drink), but preparation methods thereof are not limited to those listed above. Furthermore, kirenol or the kirenol-containing *Siegesbeckia herba* extract may be processed into a powder or a concentrate for use as a food additive. In addition, kirenol or the kirenol-containing *Siegesbeckia herba* extract may be mixed together with an active ingredient known to be effective for muscle function improvement or exercise ability enhancement to prepare a composition.

When the composition for muscle function improvement or exercise ability enhancement according to the present invention is used as a health drink composition, the health drink composition may include an additional ingredient such as one of various flavoring agents or natural carbohydrates just as an ordinary beverage does. The natural carbohydrate may be a monosaccharide such as glucose and fructose; a disaccharide such as maltose and sucrose; a polysaccharide such as dextrin and cyclodextrin; or a sugar alcohol such as xylitol, sorbitol, and erythritol. As the sweetening agent, a natural sweetening agent such as thaumatin and a stevia extract; a synthetic sweetening agent such as saccharin and aspartame, or the like may be used. The concentration of the natural carbohydrate is generally about 0.01 to 0.04 g and preferably about 0.02 to 0.03 g in 100 mL of the composition of the present invention.

Kirenol or a kirenol-containing *Siegesbeckia herba* extract may be included as an active ingredient in a food composition for muscle function improvement or exercise ability enhancement. In this case, the amount of kirenol or the kirenol-containing *Siegesbeckia herba* extract is an amount effective for accomplishing muscle function improvement or exercise ability enhancement. Although the amount of kirenol or the kirenol-containing *Siegesbeckia herba* extract is not particularly limited to a specific amount, it preferably accounts for 0.01 to 100 wt % of the total food composition.

In addition to the above, the health food of the present invention may include one or more of various nutritional supplements, vitamins, electrolytes, flavoring agents, colorants, pectic acid, salts of pectic acid, alginic acid, salts of alginic acid, organic acids, protective colloid thickeners, pH adjusting agents, stabilizers, preservatives, glycerins, alcohols, and carbonating agents. In addition, the health food of the present invention may include fruit flesh for preparing a natural fruit juice, a fruit juice drink, or a vegetable drink. Such ingredients may be used either alone or in combination. Although the concentration of such ingredients is not highly important, it is generally selected within the range of 0.01 to 0.1 parts by weight with respect to 100 parts by weight of the composition of the present invention.

Also, the present invention provides a method of improving muscle functions or enhancing exercise ability, the method including administering a composition including a *Siegesbeckia herba* extract or a fraction of the *Siegesbeckia herba* extract fraction as an active ingredient to a subject.

In one embodiment, "subject" refers to a subject in need of muscle function improvement or exercise ability enhancement. The individual may be a mammal including a human, but is not limited thereto.

In one embodiment, the *Siegesbeckia herba* extract may be an extract obtained from one or more selected from the group consisting of *Siegesbeckia glabrescens* Mak., *Siegesbeckia pubescens* Mak., and *Siegesbeckia orientalis* L.

In one embodiment, the *Siegesbeckia herba* extract may have been obtained by extracting *Siegesbeckia herba* using one or more solvents selected from the group consisting of water, organic solvents having one to six carbons, subcritical water, and supercritical fluids.

In one embodiment, the organic solvent having one to six carbons may be one or more selected from the group consisting of alcohols, acetone, ethers, benzene, chloroform, ethyl acetate, methylene chloride, hexane, cyclohexane, and petroleum ethers, all of which have one to six carbon atoms.

In one embodiment, the *Siegesbeckia herba* extract may have been obtained by extracting *Siegesbeckia herba* under ultra-high pressure conditions of 100 MPa or more.

In one embodiment, the *Siegesbeckia herba* extract fraction may have been obtained by fractionating the *Siegesbeckia herba* extract using ethyl acetate, methanol, or a solvent mixture of ethyl acetate and methanol.

In one embodiment, muscle function improvement or exercise ability enhancement may be accomplished by treating or preventing one or more diseases selected from the group consisting of atony, muscle atrophy, muscular dystrophy, muscle degeneration, myasthenia, and sarcopenia, or by improving symptoms of such a disease.

In addition, the present invention provides a method of improving muscle functions or enhancing exercise ability, the method including administering a composition including a compound represented by the following Structural Formula 1 as an active ingredient to a subject.

[Structural Formula 1]

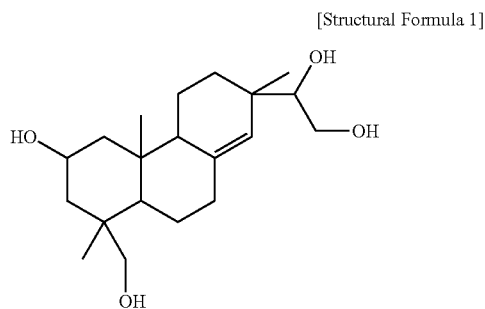 [SMILES: CC1(C(O)CO)C=C2CCC3C(C)(CO)CC(O)CC3(C)C2CC1]

In one embodiment, the compound represented by Structural Formula 1 may be kirenol, which is represented by the following Structural Formula 2:

[Structural Formula 2]

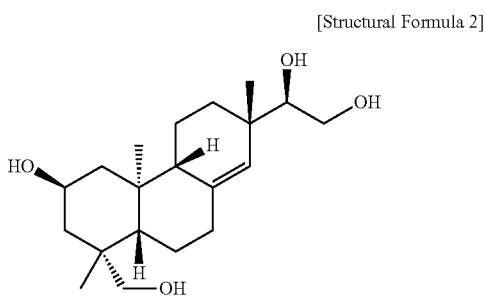

In one embodiment, "subject" refers to a subject in need of muscle function improvement or exercise ability enhancement. The individual may be a mammal including a human, but is not limited thereto.

In one embodiment, the compound represented by Structural Formula 1 may have been separated from an extract or an extract fraction obtained from one or more selected from the group consisting of *Siegesbeckia glabrescens* Mak., *Siegesbeckia pubescens* Mak., and *Siegesbeckia orientalis* L.

In one embodiment, muscle function improvement or exercise ability enhancement may be accomplished by treating or preventing one or more diseases selected from the group consisting of atony, muscle atrophy, muscular dystrophy, muscle degeneration, myasthenia, and sarcopenia, or by improving symptoms of such a disease.

The entire description that has been provided above may also be applied without limitation to methods of improving muscle functions or enhancing exercise ability by using other compositions for muscle function improvement or exercise ability enhancement.

Hereinafter, the present invention will be described in detail with reference to examples. However, the following examples are provided for illustrative purposes only so as to facilitate the understanding of the present invention, and the scope of the present invention is not limited thereto. Experimental results of the following examples are expressed in terms of mean±standard deviation. A t-test was used for statistical analysis, and a p-value equal to or less than 0.05 or 0.01 was considered to indicate statistical significance.

REFERENCE EXAMPLE 1

Material information on kirenol

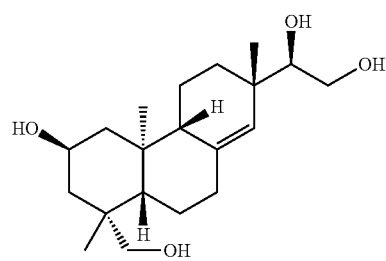

Names: Kirenol; Kirel;
(1R,3S,4aS,4bS,7S,10aS)-1,2,3,4,4a,4b,5,6,7,9,10,10a-Dodecahydro-3-hydroxy-7-[(R)-1,2-dihydroxyethyl]-1,4a,7-trimethylphenanthrene-1-methanol
CAS No.: 52659-56-0

EXAMPLE 1

Preparation of *Siegesbeckia glabrescens* Mak. Extracts

EXAMPLE 1-1

Preparation of ethanol extract of *Siegesbeckia glabrescens* Mak

Leaves and stems of dried *Siegesbeckia glabrescens* Mak. were crushed using a blender, 100 g of the crushed *Siegesbeckia glabrescens* Mak. sample was put in 1 L ethanol, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethanol extract of *Siegesbeckia glabrescens* Mak.

EXAMPLE 1-2

Preparation of hot-water extract of *Siegesbeckia glabrescens* Mak

Leaves and stems of dried *Siegesbeckia glabrescens* Mak. were crushed using a blender, 100 g of the crushed *Siegesbeckia glabrescens* Mak. sample was put in 1 L water, and the mixture was extracted while being stirred at 100° C. for four hours. The extracted sample was filtered using Whatman No. 2 filter paper, and the solvent was removed by concentrating the filtered extract with a vacuum rotary concentrator to obtain a hot-water extract of *Siegesbeckia glabrescens* Mak.

EXAMPLE 1-3

Preparation of hexane extract of *Siegesbeckia glabrescens* Mak

Leaves and stems of dried *Siegesbeckia glabrescens* Mak. were crushed using a blender, 100 g of the crushed *Siegesbeckia glabrescens* Mak. sample was put in 1 L hexane, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain a hexane extract of *Siegesbeckia glabrescens* Mak.

EXAMPLE 1-4

Preparation of ethyl acetate extract of *Siegesbeckia glabrescens* Mak

Leaves and stems of dried *Siegesbeckia glabrescens* Mak. were crushed using a blender, 100 g of the crushed *Siegesbeckia glabrescens* Mak. sample was put in 1 L ethyl acetate, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethyl acetate extract of *Siegesbeckia glabrescens* Mak.

EXAMPLE 1-5

Preparation of ultra-high pressure extract of *Siegesbeckia glabrescens* Mak.

Leaves and stems of dried *Siegesbeckia glabrescens* Mak. were crushed using a blender, 1 g of the crushed *Siegesbeckia glabrescens* Mak. sample and 76 mL of 18% ethanol were put in a polyethylene bag, the bag was sealed, and then the mixture was extracted using an ultra-high pressure extraction device (Frescal MFP-7000; Mitsubishi Heavy Industries, Tokyo, Japan). Ultra-high pressure extraction conditions included an extraction pressure of 320 MPa and extraction time of five minutes. The extracted sample was filtered using Whatman No. 2 filter paper, and the solvent was removed by concentrating the filtered extract with a vacuum rotary concentrator to obtain an ultra-high pressure extract of *Siegesbeckia glabrescens* Mak.

EXAMPLE 1-6

Preparation of supercritical-fluid extract of *Siegesbeckia glabrescens* Mak

Leaves and stems of dried *Siegesbeckia glabrescens* Mak. were crushed using a blender, 1 g of the crushed *Siegesbeckia glabrescens* Mak. sample was charged into a sample cartridge, and the sample was extracted using a supercritical-fluid extraction device (SFX 3560, Isco Inc., Lincoln, Nebr., USA). Supercritical-fluid extraction conditions included an extraction pressure of 20 MPa, an extraction temperature of 60° C., a supercritical carbon dioxide flow rate of 60 mL/min, and extraction time of 60 minutes. When the supercritical-fluid extraction was completed, the supercritical state of the fluid was deactivated by lowering the pressure of the extraction device, and thus a supercritical-fluid extract of *Siegesbeckia glabrescens* Mak. was obtained.

EXAMPLE 1-7

Preparation of subcritical water extract of *Siegesbeckia glabrescens* Mak

Leaves and stems of dried *Siegesbeckia glabrescens* Mak. were crushed using a blender, 1 g of the crushed *Siegesbeckia glabrescens* Mak. sample was put in 10 mL distilled water, and the sample was extracted using a subcritical water extraction device (DIONEX Accelerated Solvent Extractor 100, DIONEX Co., USA). Subcritical water extraction was conducted under subcritical water extraction conditions that included an extraction pressure of 0.5 MPa, an extraction temperature of 240° C., and extraction time of 20 minutes. The extracted sample was filtered using Whatman No. 2 filter paper, and the filtered extract was freeze-dried at −40° C. to obtain a subcritical water extract of *Siegesbeckia glabrescens* Mak.

EXAMPLE 2

Preparation of *Siegesbeckia pubescens* Mak. Extracts

EXAMPLE 2-1

Preparation of ethanol extract of *Siegesbeckia pubescens* Mak

Leaves and stems of dried *Siegesbeckia pubescens* Mak. were crushed using a blender, 100 g of the crushed *Siegesbeckia pubescens* Mak. sample was put in 1 L ethanol, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethanol extract of *Siegesbeckia pubescens* Mak.

EXAMPLE 2-2

Preparation of hot-water extract of *Siegesbeckia pubescens* Mak

Leaves and stems of dried *Siegesbeckia pubescens* Mak. were crushed using a blender, 100 g of the crushed *Siegesbeckia pubescens* Mak. sample was put in 1 L water, and the mixture was extracted while being stirred at 100° C. for four hours. The extracted sample was filtered using Whatman No. 2 filter paper, and the solvent was removed by concentrating the filtered extract with a vacuum rotary concentrator to obtain a hot-water extract of *Siegesbeckia pubescens* Mak.

EXAMPLE 2-3

Preparation of hexane extract of *Siegesbeckia pubescens* Mak

Leaves and stems of dried *Siegesbeckia pubescens* Mak. were crushed using a blender, 100 g of the crushed *Siegesbeckia pubescens* Mak. sample was put in 1 L hexane, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain a hexane extract of *Siegesbeckia pubescens* Mak.

EXAMPLE 2-4

Preparation of ethyl acetate extract of *Siegesbeckia pubescens* Mak

Leaves and stems of dried *Siegesbeckia pubescens* Mak. were crushed using a blender, 100 g of the crushed *Siegesbeckia pubescens Mak. sample was put in 1 L ethyl acetate, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethyl acetate extract of *Siegesbeckia pubescens* Mak.

EXAMPLE 2-5

Preparation of ultra-high pressure extract of *Siegesbeckia pubescens* Mak

Leaves and stems of dried *Siegesbeckia pubescens* Mak. were crushed using a blender, 1 g of the crushed *Siegesbeckia pubescens* Mak. sample and 76 mL of 18% ethanol were put in a polyethylene bag, the bag was sealed, and then the mixture was extracted using an ultra-high pressure extraction device (Frescal MFP-7000; Mitsubishi Heavy Industries, Tokyo, Japan). Ultra-high pressure extraction conditions included an extraction pressure of 320 MPa and extraction time of five minutes. The extracted sample was filtered using Whatman No. 2 filter paper, and the solvent was removed by concentrating the filtered extract with a vacuum rotary concentrator to obtain an ultra-high pressure extract of *Siegesbeckia pubescens* Mak.

EXAMPLE 2-6

Preparation of supercritical-fluid extract of *Siegesbeckia pubescens* Mak

Leaves and stems of dried *Siegesbeckia pubescens* Mak. were crushed using a blender, 1 g of the crushed *Siegesbeckia pubescens* Mak. sample was charged into a sample cartridge, and the sample was extracted using a supercritical-fluid extraction device (SFX 3560, Isco Inc., Lincoln, Nebr., USA). Supercritical-fluid extraction conditions included an extraction pressure of 50 MPa, an extraction temperature of 40° C., a supercritical carbon dioxide flow rate of 60 mL/min, and extraction time of 60 minutes. When the supercritical-fluid extraction was completed, the supercritical state of the fluid was deactivated by lowering the pressure of the extraction device, and thus a supercritical-fluid extract of *Siegesbeckia pubescens* Mak. was obtained.

EXAMPLE 2-7

Preparation of subcritical water extract of *Siegesbeckia pubescens* Mak

Leaves and stems of dried *Siegesbeckia pubescens* Mak. were crushed using a blender, 1 g of the crushed *Siegesbeckia pubescens* Mak. sample was put in 10 mL distilled water, and the sample was extracted using a subcritical water extraction device (DIONEX Accelerated Solvent Extractor 100, DIONEX Co., USA). Subcritical water extraction was conducted under subcritical water extraction conditions that included an extraction pressure of 5 MPa, an extraction temperature of 90° C., and extraction time of 15 minutes. The extracted sample was filtered using Whatman No. 2 filter paper, and the filtered extract was freeze-dried at −40° C. to obtain a subcritical water extract of *Siegesbeckia pubescens* Mak.

EXAMPLE 3

Preparation of *Siegesbeckia orientalis* L. extracts

EXAMPLE 3-1

Preparation of ethanol extract of *Siegesbeckia orientalis*

Leaves and stems of dried *Siegesbeckia orientalis* L. were crushed using a blender, 100 g of the crushed *Siegesbeckia orientalis* L. sample was put in 1 L ethanol, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethanol extract of *Siegesbeckia orientalis* L.

EXAMPLE 3-2

Preparation of hot-water extract of *Siegesbeckia orientalis* L

Leaves and stems of dried *Siegesbeckia orientalis* L. were crushed using a blender, 100 g of the crushed *Siegesbeckia orientalis* L. sample was put in 1 L water, and the mixture was extracted while being stirred at 100 ° C. for four hours. The extracted sample was filtered using Whatman No. 2 filter paper, and the solvent was removed by concentrating the filtered extract with a vacuum rotary concentrator to obtain a hot-water extract of *Siegesbeckia orientalis* L.

EXAMPLE 3-3

Preparation of hexane extract of *Siegesbeckia orientalis* L

Leaves and stems of dried *Siegesbeckia orientalis* L. were crushed using a blender, 100 g of the crushed *Siegesbeckia orientalis* L. sample was put in 1 L hexane, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain a hexane extract of *Siegesbeckia orientalis* L.

EXAMPLE 3-4

Preparation of ethyl acetate extract of *Siegesbeckia orientalis* L

Leaves and stems of dried *Siegesbeckia orientalis* L. were crushed using a blender, 100 g of the crushed *Siegesbeckia orientalis* L. sample was put in 1 L ethyl acetate, and the mixture was extracted while being stirred at 50° C. for 60 minutes. The extracted sample was filtered using Whatman No. 2 filter paper, and the solvent was removed by concentrating the filtered extract with a vacuum rotary concentrator to obtain an ethyl acetate extract of *Siegesbeckia orientalis* L.

EXAMPLE 3-5

Preparation of ultra-high pressure extract of *Siegesbeckia orientalis* L

Leaves and stems of dried *Siegesbeckia orientalis* L. were crushed using a blender, 1 g of the crushed *Siegesbeckia*

*orientalis* L. sample and 76 mL of 18% ethanol were put in a polyethylene bag, the bag was sealed, and then the mixture was extracted using an ultra-high pressure extraction device (Frescal MFP-7000; Mitsubishi Heavy Industries, Tokyo, Japan). Ultra-high pressure extraction conditions included an extraction pressure of 320 MPa and extraction time of five minutes. The extracted sample was filtered using Whatman No. 2 filter paper, and the solvent was removed by concentrating the filtered extract with a vacuum rotary concentrator to obtain an ultra-high pressure extract of *Siegesbeckia orientalis* L.

EXAMPLE 3-6

Preparation of supercritical-fluid extract of *Siegesbeckia orientalis* L

Leaves and stems of dried *Siegesbeckia orientalis* L. were crushed using a blender, 1 g of the crushed *Siegesbeckia orientalis* L. sample was charged into a sample cartridge, and the sample was extracted using a supercritical-fluid extraction device (SFX 3560, Isco Inc., Lincoln, Nebr., USA). Supercritical-fluid extraction conditions included an extraction pressure of 40 MPa, an extraction temperature of 50° C., a supercritical carbon dioxide flow rate of 60 mL/min, and extraction time of 60 minutes. When the supercritical-fluid extraction was completed, the supercritical state of the fluid was deactivated by lowering the pressure of the extraction device, and thus a supercritical-fluid extract of *Siegesbeckia orientalis* L. was obtained.

EXAMPLE 3-7

Preparation of subcritical water extract of *Siegesbeckia orientalis* L

Leaves and stems of dried *Siegesbeckia orientalis* L. were crushed using a blender, 1 g of the crushed *Siegesbeckia orientalis* L. sample was put in 10 mL distilled water, and the sample was extracted using a subcritical water extraction device (DIONEX Accelerated Solvent Extractor 100, DIONEX Co., USA). Subcritical water extraction was conducted under subcritical water extraction conditions that included an extraction pressure of 2.5 MPa, an extraction temperature of 150° C., and extraction time of 15 minutes. The extracted sample was filtered using Whatman No. 2 filter paper, and the filtered extract was freeze-dried at −40° C. to obtain a subcritical water extract of *Siegesbeckia orientalis* L.

EXAMPLE 4

Separation and structural determination of kirenol

EXAMPLE 4-1

Separation of kirenol

The concentrated ethanol extract of *Siegesbeckia orientalis* L. obtained from the above Example 3-1 was loaded into a column filled with silica gel, and the extract was fractionated using a solvent system of ethyl acetate and methanol mixed in a ratio of 10:0.5 (v/v). The extract was separated into a total of seven fractions according to the order of fractionation, and each fraction was concentrated and dried. The sixth fraction (Fraction No. 6) among the seven fractions was fractionated using RP-18 reverse phase column chromatography (Lichroprep RP-18 25~40 μm, Merck&Co., Whitehouse Station, N.J., USA) and 10% ethyl acetate, which is a developing solvent. Fraction No. 6 was separated into a total of two fractions according to the order of fractionation, and each fraction was concentrated by drying. The second fraction (Fraction No. 6-2) among the two fractions was concentrated by drying, and was fractionated again using RP-18 reverse phase column chromatography and 20% ethyl acetate, which is a developing solvent. Fraction No. 6-2 was separated into a total of three fractions according to the order of fractionation, and each fraction was concentrated by drying. Finally, the second fraction (Fraction No. 6-2-2) among the three fractions was concentrated by drying to isolate a single pure active substance.

EXAMPLE 4-2

Structural determination of kirenol

For structural determination of the single active substance separated according to the above Example 4-1, the $^1$H-NMR spectrum at 500 MHz and the $^{13}$C-NMR spectrum at 125 MHz (solvent: MeOH) were acquired. To investigate an $^1$H$^1$H correlation and a $^1$H$^{13}$C correlation based on the acquired $^1$H-NMR spectrum and $^{13}$C-NMR spectrum, the $^1$H$^1$H COSY spectrum and the $^1$H$^{13}$C HSQC spectrum were acquired, each carbon signal was distinguished by the wavelength generated from carbon resonance, and the results were recorded.

Also, FAB-MS was conducted for the mass analysis of the single active substance that had been separated. As [M] was observed at m/z 338.48 according to FAB-MS, the present compound was found to have a molecular weight of 338.48, and the molecular formula of the compound was $C_{20}H_{34}O_4$.

When the results of $^1$H-NMR, $^{13}$C-NMR, and FAB-MS were compared to a previously published research report (Wang J. P. et al., Pharmacogn. Mag., 8:149-155, 2012), the single active substance that had been separated was identified as a kirenol compound represented by the following Structural Formula 2.

[Structural Formula 2]

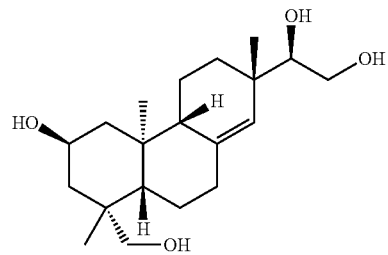

EXAMPLE 5

Increased protein expression of p-mTOR, which is major gene involved in muscle functions

EXAMPLE 5-1

Effect of kirenol or kirenol-containing ethanol extracts of *Siegesbeckia glabrescens* Mak., *Siegesbeckia pubescens* Mak., and *Siegesbeckia orientalis* L. on muscle function improvement L6 myoblasts (American Type Culture Collection, Manassas, Va., USA), which are muscle cells, were incubated in Dulbecco's Modified Eagle's Medium (DMEM; Hyclone) containing 10% fetal bovine serum (FBS; Hyclone, Logan, Utah, USA), 100 U/mL penicillin, and 100 μg/mL streptomycin (Gibco, Grand Island, N.Y., USA). The L6 cells were treated with the *Siegesbeckia glabrescens* Mak. ethanol extract prepared according to the above Example 1-1, the *Siegesbeckia pubescens* Mak. ethanol extract prepared according to Example 2-1, or the *Siegesbeckia orientalis* L. ethanol extract prepared according to Example 3-1, each at a concentration of 10 ppm. Also, L6 cells were treated with 10 μM kirenol prepared according to Example 4. In this case, a group treated with 0.01% DMSO instead of being treated with a sample was prepared as a control group. 24 hours later, the L6 cells were dissolved in a RIPA (ELPIS-Biotech, Daejeon, Korea) buffer solution containing a proteinase inhibitor cocktail (Sigma-Aldrich, St. Louis, Mo., USA). The samples were boiled for five minutes, and then an identical amount of protein (20 μg) was separated using 10% SDS-PAGE for electrophoresis. After electrophoresis, the proteins that had been separated were transferred onto a nitrocellulose membrane and western blotting was performed. The proteins were reacted with a primary antibody, and were washed three times for ten minutes using Tris-buffered saline containing 0.1% Tween 20 (TBST). In this case, the primary antibody used in the present invention was diluted at a ratio of 1:1000. A secondary antibody (anti-rabbit horseradish) was added onto the membrane that had been subjected to the primary antibody reaction, and then a secondary antibody reaction was carried out for two hours at room temperature. In this case, the secondary antibody was diluted at a ratio of 1:5000. The protein bands were colored with ECL western blotting detection reagents (Amersham, Tokyo, Japan) for the confirmation of the protein expression of p-mTOR, which is a major gene concerned with muscle functions, and α-tubulin was used to indicate that a constant amount of protein was loaded into each lane.

As shown in FIG. 1, the protein expression level of p-mTOR, which is a major gene concerned with muscle functions, increased as a result of treatment with kirenol or a kirenol-containing ethanol extract of *Siegesbeckia glabrescens* Mak., *Siegesbeckia pubescens* Mak., or *Siegesbeckia orientalis* L.

Such results indicate that kirenol, a *Siegesbeckia herba* extract containing kirenol, or a fraction of the *Siegesbeckia herba* extract according to the present invention exhibits an activity of increasing muscle mass by increasing the p-mTOR protein expression level.

EXAMPLE 5-2

Effect of ultra-high pressure extract of *Siegesbeckia orientalis* L. on muscle function improvement The ultra-high pressure extract of *Siegesbeckia orientalis* L. prepared according to Example 3-5 was used to treat muscle cells in the same manner as in Example 5-1. In this case, the concentration of the ultra-high pressure extract was set at 10, 20, or 40 ppm.

Figure 2:
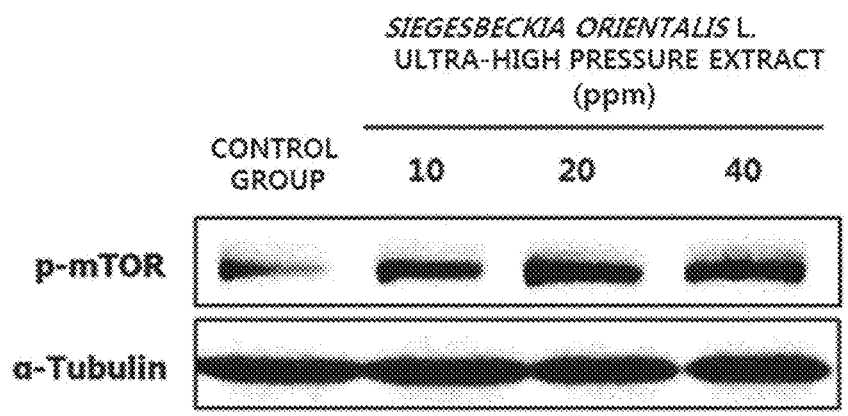
FIG. 2 shows the measurement of p-mTOR protein expression levels in L6 muscle cells after treatment with a kirenol-containing, ultra-high pressure extract of *Siegesbeckia orientalis* L.

As shown in FIG. 2, the protein expression level of p-mTOR, which is a major gene concerned with muscle functions, increased as a result of treatment with a kirenol-containing ultra-high pressure extract of *Siegesbeckia orientalis* L.

Such results indicate that kirenol, a *Siegesbeckia herba* extract containing kirenol, or a fraction of the *Siegesbeckia herba* extract according to the present invention exhibits an activity of increasing muscle mass by increasing the p-mTOR protein expression level.

EXAMPLE 5-3

Effect of ethyl acetate extract of *Siegesbeckia herba* on muscle function improvement Each of the ethyl acetate extract of *Siegesbeckia glabrescens* Mak. prepared according to Example 1-4, the ethyl acetate extract of *Siegesbeckia pubescens* Mak. prepared according to Example 2-4, and the ethyl acetate extract of *Siegesbeckia orientalis* L. prepared according to Example 3-4 was used to treat muscle cells in the same manner as in Example 5-1. In this case, the concentrations of the ethyl acetate extracts were set at 10 ppm.

ECL western blotting detection reagents (Amersham, Tokyo, Japan) were used to color p-mTOR protein bands, and the G:BOX EF imaging system (Syngene, Cambridge, UK) was used to measure the densities of the colored protein bands. In this case, relative densities of protein bands of experimental groups treated with a sample were determined as a percentage (%), with the density of the control protein band being 100%.

The results are provided in the following FIG. 1:

TABLE 1

Effect of ethyl acetate extracts of *Siegesbeckia* herba on increasing p-mTOR protein expression level

| Groups | Relative density (%) |
|---|---|
| Control group | 100 |
| Example 1-4 | 125 |
| Example 2-4 | 130 |
| Example 3-4 | 141 |

As shown in Table 1, ethyl acetate extracts of *Siegesbeckia glabrescens* Mak., *Siegesbeckia pubescens* Mak., and *Siegesbeckia orientalis* L. increase the protein expression level of p-mTOR, which is a major gene concerned with muscle function improvement.

Such results indicate that kirenol, a *Siegesbeckia herba* extract containing kirenol, or a fraction of the *Siegesbeckia herba* extract according to the present invention exhibits an activity of increasing muscle mass by increasing the p-mTOR protein expression level.

EXAMPLE 5-4

Effect of supercritical extracts and subcritical extracts of *Siegesbeckia herba* on muscle function improvement Each of the supercritical extract and subcritical extract of *Siegesbeckia glabrescens* Mak. prepared according to Examples 1-6 and 1-7, the supercritical extract and subcritical extract of *Siegesbeckia pubescens* Mak. prepared according to Examples 2-6 and 2-7, and the supercritical extract and subcritical extract of *Siegesbeckia orientalis* L. prepared according to Examples 3-6 and 3-7 was used to treat muscle cells in the same manner as in Example 5-1. In this case, the concentrations of the extracts were set at 20 ppm. Then, relative densities of protein bands of experimental groups treated with a sample were determined as a percentage (%) in the same manner as in Example 5-3, with the density of the control protein band being 100%.

The results are provided in the following Table 2:

TABLE 2

Effect of supercritical extracts and subcritical extracts of
Siegesbeckia herba on increasing p-mTOR protein expression level

| Groups | Relative density (%) |
|---|---|
| Control group | 100 |
| Example 1-6 | 116 |
| Example 1-7 | 138 |
| Example 2-6 | 130 |
| Example 2-7 | 139 |
| Example 3-6 | 128 |
| Example 3-7 | 146 |

As shown in Table 2, supercritical extracts and subcritical extracts of *Siegesbeckia glabrescens* Mak., *Siegesbeckia pubescens* Mak., and *Siegesbeckia orientalis* L. increase the protein expression level of p-mTOR, which is a major gene concerned with muscle function improvement.

Such results indicate that kirenol, a *Siegesbeckia herba* extract containing kirenol, or a fraction of the *Siegesbeckia herba* extract according to the present invention exhibits an activity of increasing muscle mass by increasing the p-mTOR protein expression level.

EXAMPLE 5-5

Effect of ethanol extract fraction of *Siegesbeckia orientalis* L. on muscle function improvement Fraction No. 6, which had been obtained by fractionating the *Siegesbeckia orientalis* L. ethanol extract of Example 4-1 using a solvent mixture of ethyl acetate and methanol mixed at 10:0.5 (v/v), was used to treat muscle cells in the same manner as in Example 5-1. In this case, the concentration of Fraction No. 6 was set at 20 ppm. Then, the relative density of protein bands of the experimental group treated with a sample was determined as a percentage (%) in the same manner as in Example 5-3, with the density of the control protein band being 100%.

The result shows that the relative density of the fraction of the *Siegesbeckia orientalis* L. ethanol extract is 126% with respect to the control group, indicating an increase in the protein expression level of p-mTOR, which is a major gene concerned with muscle function improvement.

Such a result indicates that kirenol, a *Siegesbeckia herba* extract containing kirenol, or a fraction of the *Siegesbeckia herba* extract according to the present invention exhibits an activity of increasing muscle mass by increasing the p-mTOR protein expression level.

EXAMPLE 6

Effectiveness on increasing muscle differentiation and anabolism, and reducing catabolism

EXAMPLE 6-1

Effectiveness on increasing muscle differentiation and anabolism

L6 myoblasts (American Type Culture Collection, Manassas, Va., USA), which are muscle cells, were incubated in DMEM (10% FBS, 100 U/mL penicillin, 100 µg/mL streptomycin). When the cell density reached about 80~85%, the cell culture medium was replaced with a DMEM growth medium supplemented with 2% FBS. The experiment was initiated after 6 days of differentiation. To induce muscle reduction, the differentiated L6 cells were treated with TNF-α for 24 hours and then with the ethanol extract of *Siegesbeckia orientalis* L. (10, 40 ppm) prepared according to Example 3-1 and kirenol (10, 40 µM) prepared according to Example 4. RT-PCR was carried out to measure mRNA expression levels of myogenin and MyoD, which are muscle differentiation regulatory factors. TRIzol Reagent (Invitrogen, Carlsbad, Calif., USA) was used for harvesting total RNA from the differentiated cells, and the total RNA was reverse transcribed. The RT-PCR analysis was carried out as follows: First, the RNA was reverse transcribed for cDNA synthesis by using a reverse transcriptase. RT-PCR was conducted using specific primers as listed below, and β-actin was used to indicate that a constant amount of mRNA was loaded into each lane.

```
Myogenin:
(Forward primer)
SEQ ID NO: 1:
5'-TGGGCTGCCACAAGCCAGAC-3'

(Reverse primer)
SEQ ID NO: 2:
5'-CAGCCCAGCCACTGGCATCA-3'

MyoD:
(Forward primer)
SEQ ID NO: 3:
5'-GGATGGTGCCCCTGGGTCCT-3'

(Reverse primer)
SEQ ID NO: 4:
5'-TGGCCTTCGCTGTGAGTCGC-3'

β-actin:
(Forward primer)
SEQ ID NO: 5:
5'-AGCCATGTACGTAGCCATCC-3'

(Reverse primer)
SEQ ID NO: 6:
5'-CTCTCAGCTGTGGTGGTGAA-3'
```

Figure 3:
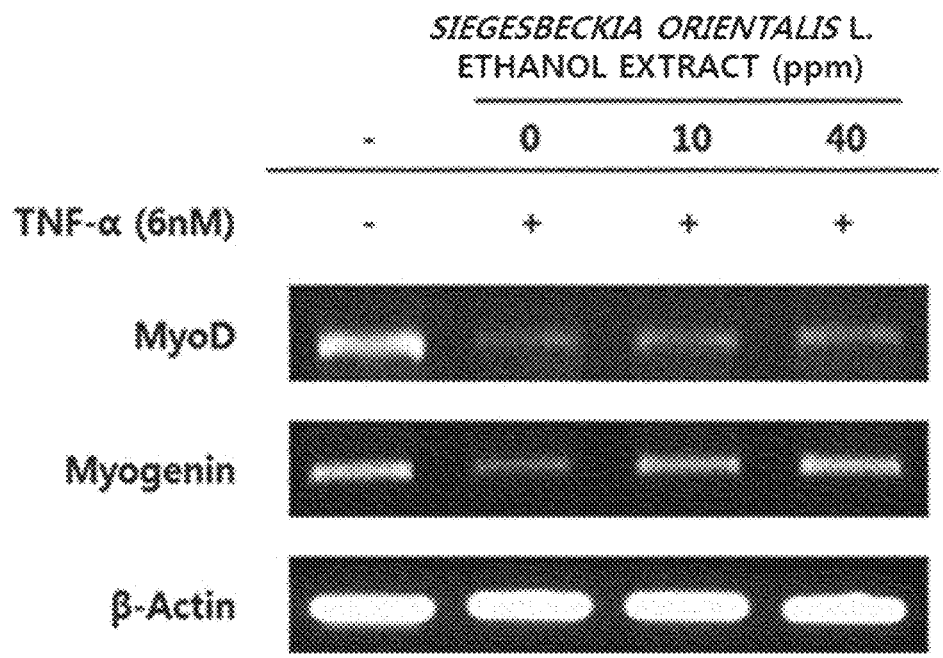
FIG. 3 shows the measurement of mRNA expression levels of muscle differentiation regulatory genes (myogenin and MyoD) in L6 muscle cells after treatment with a kirenol-containing ethanol extract of *Siegesbeckia orientalis* L.
Figure 4:
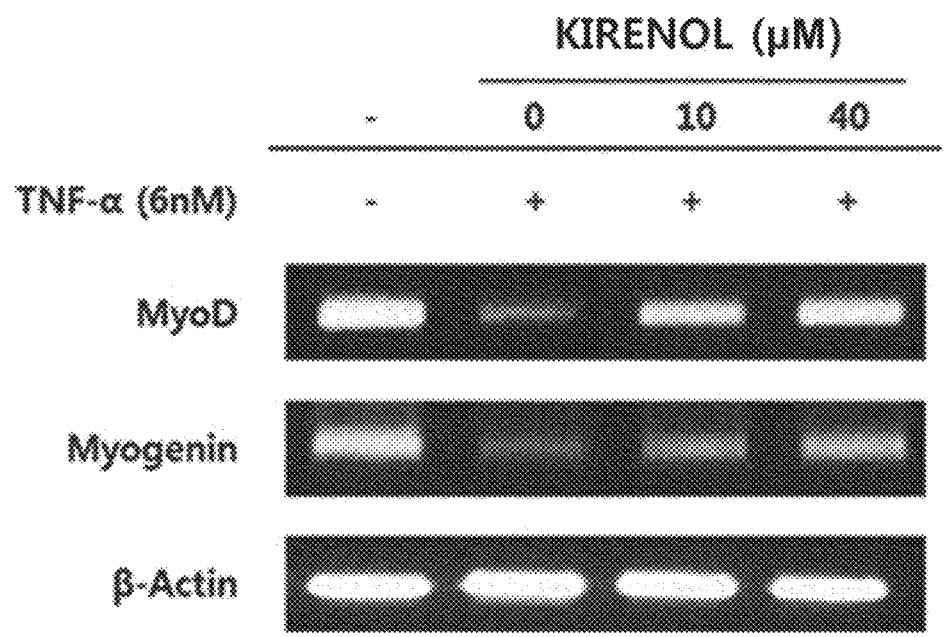
FIG. 4 shows the measurement of mRNA expression levels of muscle differentiation regulatory genes (myogenin and MyoD) in L6 muscle cells after treatment with kirenol.

As shown in FIGS. 3 and 4, kirenol or the ethanol extract of *Siegesbeckia orientalis* L. increases mRNA expression levels of myogenin and MyoD, which are muscle differentiation regulatory factors.

Such results indicate that kirenol, a *Siegesbeckia herba* extract containing kirenol, or a fraction of the *Siegesbeckia herba* extract according to the present invention contributes to muscle formation by increasing muscle differentiation and muscle anabolism.

EXAMPLE 6-2

Effectiveness on reducing muscle catabolism

Total RNA was harvested from differentiated cells in the same manner as in Example 3-1, the total RNA was reverse transcribed, and then RT-PCR was performed. In this case, the ethanol extract (10, 40 ppm) of *Siegesbeckia orientalis* L. prepared according to Example 3-1 and kirenol (10, 40 µM) prepared according to Example 4 were used for treatment. RT-PCR was carried out using specific primers as listed below.

```
Atrogin-1:
(Forward primer)
SEQ ID NO: 7:
5'-CCCTGAGTGGCATCGCCCAA-3'

(Reverse primer)
SEQ ID NO: 8:
5'-AGGTCCCGCCCATCGCTCA-3'

MuRF1:
(Forward primer)
SEQ ID NO: 9:
5'-TCTACTCGGCCACAGGCGCT-3'

(Reverse primer)
SEQ ID NO: 10:
5'-CTTGACAGCTCCCGCCGCAA-3'
```

Figure 5:
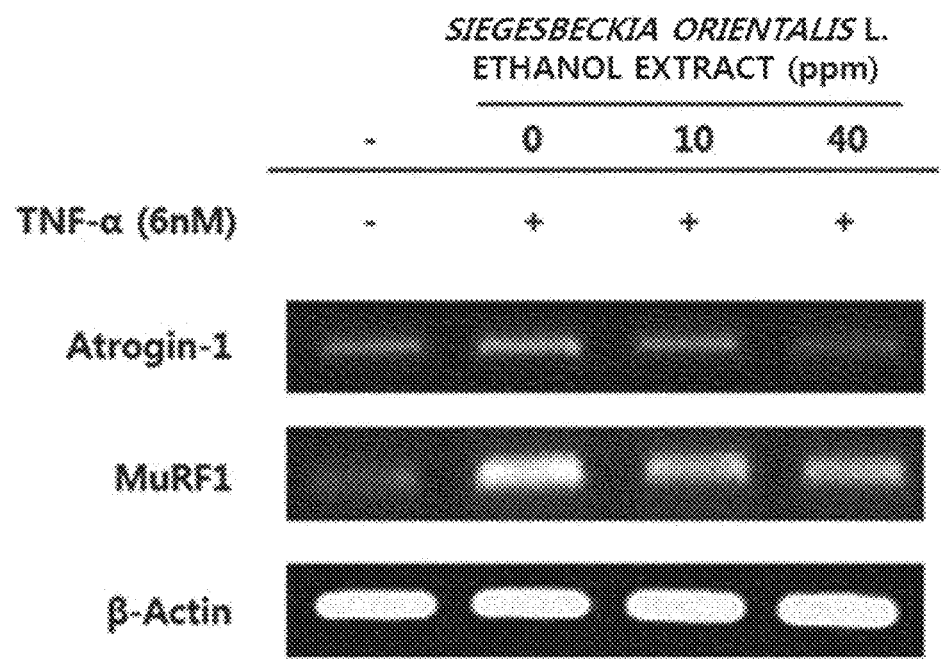
FIG. 5 shows the measurement of mRNA expression levels of atrogin-1 and MuRF1, which are major genes concerned with intramuscular protein catabolism, in L6 muscle cells after treatment with a kirenol-containing ethanol extract of *Siegesbeckia orientalis* L.
Figure 6:
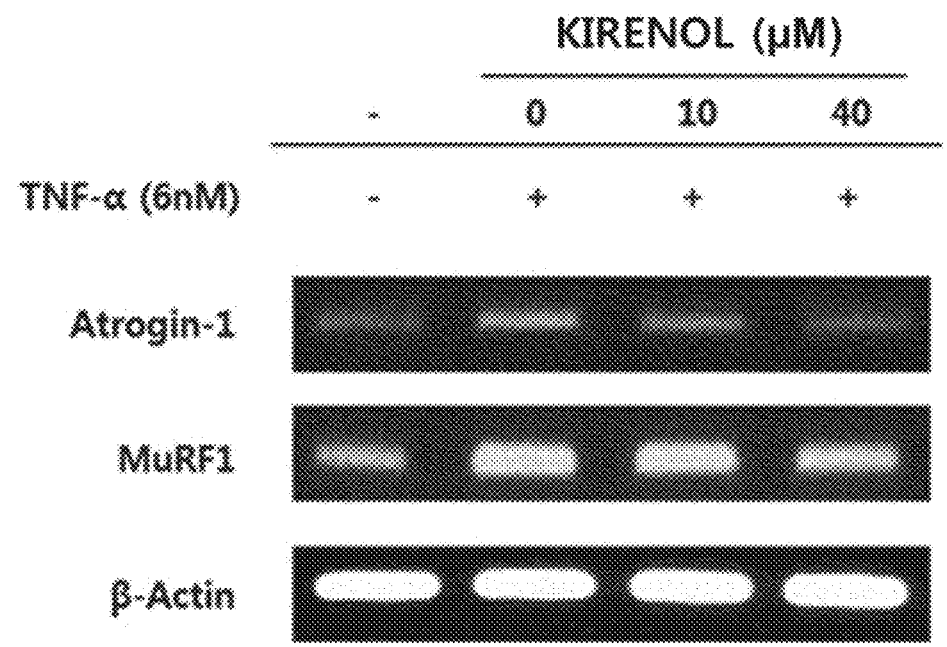
FIG. 6 shows the measurement of mRNA expression levels of atrogin-1 and MuRF1, which are major genes concerned with intramuscular protein catabolism, in L6 muscle cells after treatment with kirenol.

As shown in FIGS. 5 and 6, kirenol or an ethanol extract of *Siegesbeckia orientalis* L. reduces mRNA expression levels of atrogin-1 and MuRF1, which are major ligases concerned with intramuscular protein catabolism.

Such results indicate that kirenol, a kirenol-containing *Siegesbeckia herba* extract, or a fraction of the *Siegesbeckia herba* extract contributes to maintaining muscle mass by inhibiting muscle catabolism concerned with muscle loss.

EXAMPLE 7

Confirmation of increase in muscle mass in normal-diet animal model

EXAMPLE 7-1

Test animal diet

Four-week-old male C57BL/6 mice were adapted for one week and were provided with a normal diet (Research Diets D12450B, 10% kcal from fat, New Brunswick, N.J., USA). For the experiment, the mice were divided randomly into a total of three groups with five mice per group on the basis of body weight. The *Siegesbeckia orientalis* L. ethanol extract prepared according to Example 3-1 was suspended in 0.25% carboxymethyl cellulose, and the suspension was orally administered to an experimental group at a concentration of 250 mg of *Siegesbeckia orientalis* L. ethanol extract/day/kg body weight once a day at a constant time for six weeks. The control group was orally administered only the same amount of 0.25% carboxymethyl cellulose. The dietary dose and weight of the mice to which a sample was administered were measured once every week.

EXAMPLE 7-2

Effectiveness on increasing muscle mass

Calf muscle from both legs of the normal diet mice according to Example 7-1 were removed and were weighed using a microbalance (Mettler PE160, USA). The statistical significance of the test results were verified by conducting a t-test on results obtained from the normal diet group and *Siegesbeckia orientalis* L. ethanol extract administration group, and a statistically significant difference was observed (**p<0.01).

Figure 7:
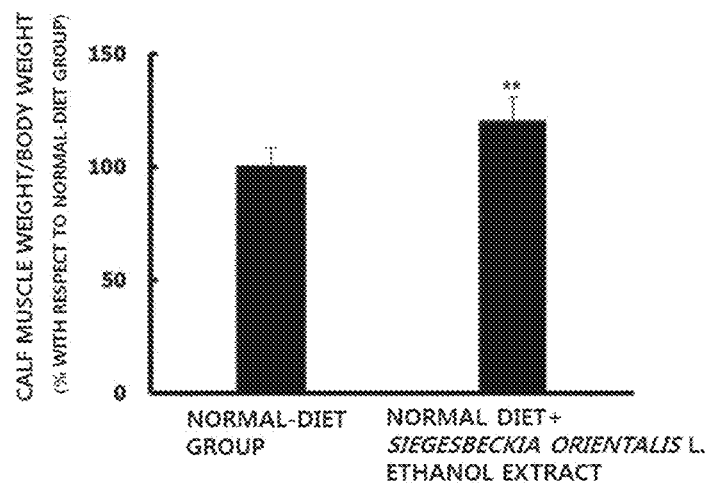
FIG. 7 shows the measurement of an increase in muscle mass in a normal-diet animal model after the administration of a kirenol-containing ethanol extract of *Siegesbeckia orientalis* L.

As shown in FIG. 7, the group administered the *Siegesbeckia orientalis* L. ethanol extract exhibited a 23% increase in muscle weight as compared to the control group.

Such results indicate that kirenol, a kirenol-containing *Siegesbeckia herba* extract, or a fraction of the *Siegesbeckia herba* extract according to the present invention is effective for increasing muscle mass.

EXAMPLE 7-3

Effectiveness on increasing muscle volume

Final muscle volumes of the normal diet mice of Example 7-1 were measured using micro-positron emission tomography/computed tomography (micro-PET/CT, INVEON, Siemens, USA).

Figure 8:
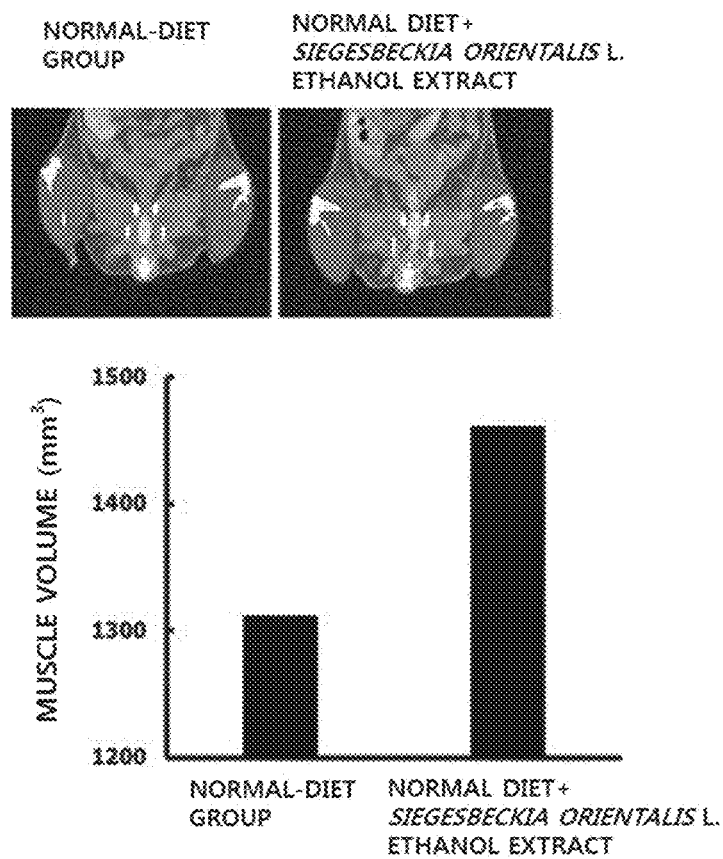
FIG. 8 shows the measurement of an increase in muscle volume in a normal-diet animal model after the administration of a kirenol-containing ethanol extract of *Siegesbeckia orientalis* L. (left: PET/CT result, right: muscle volume measurement result)

As shown in FIG. 8, the group administered the *Siegesbeckia orientalis* L. ethanol extract exhibited an 11.4% increase in muscle volume as compared to the control group.

Such results indicate that kirenol, a kirenol-containing *Siegesbeckia herba* extract, or a fraction of the *Siegesbeckia herba* extract according to the present invention is effective for increasing muscle mass by increasing muscle volume.

EXAMPLE 7-4

Effectiveness of hot-water extract of *Siegesbeckia herba* on increasing muscle mass Muscle masses after treatment with each of the hot-water extract of *Siegesbeckia glabrescens* Mak. prepared according to Example 1-2, hot-water extract of *Siegesbeckia pubescens* Mak. prepared according to Example 2-2, and hot-water extract of *Siegesbeckia orientalis* L. prepared according to Example 3-2 were measured in the same manner as in Examples 7-1 and 7-2.

The results are provided in the following Table 3:

TABLE 3

Effectiveness of hot-water extract of *Siegesbeckia herba* on increasing muscle mass

| Groups | Relative density (%) |
|---|---|
| Control group | 100 |
| Example 1-2 | 118 ± 3.7** |
| Example 2-2 | 115 ± 5.1* |
| Example 3-2 | 121 ± 4.3** |

*p < 0.05;
**p < 0.01

As shown in Table 3, the muscle mass significantly increased in groups administered the hot-water extract of *Siegesbeckia glabrescens* Mak., *Siegesbeckia pubescens* Mak., or *Siegesbeckia orientalis* L. as compared to the control group.

Such results indicate that kirenol, a kirenol-containing *Siegesbeckia herba* extract, or a fraction of the *Siegesbeckia herba* extract according to the present invention is effective for increasing muscle mass.

EXAMPLE 8

Confirmation of increase in muscle mass in high-fat diet animal model

EXAMPLE 8-1

Test animal diet

Four-week-old male C57BL/6 mice were adapted for one week and were provided with a high-fat diet (Research Diets D12492, 60% kcal from fat) for six weeks to induce obesity. The mice were divided randomly into a total of two groups with five mice per group, and were subjected to oral administration in the same manner as in Example 7-1.

EXAMPLE 8-2

Effectiveness on increasing muscle mass

Calf muscle from both legs of the high-fat diet mice according to Example 8-1 were removed and were weighed in the same manner as in Example 7-2. The statistical significance of the test results were verified by conducting a t-test on results obtained from the high-fat diet group and high-fat diet group administered the *Siegesbeckia orientalis* L. ethanol extract, and a statistically significant difference was observed (**p<0.01).

Figure 9:
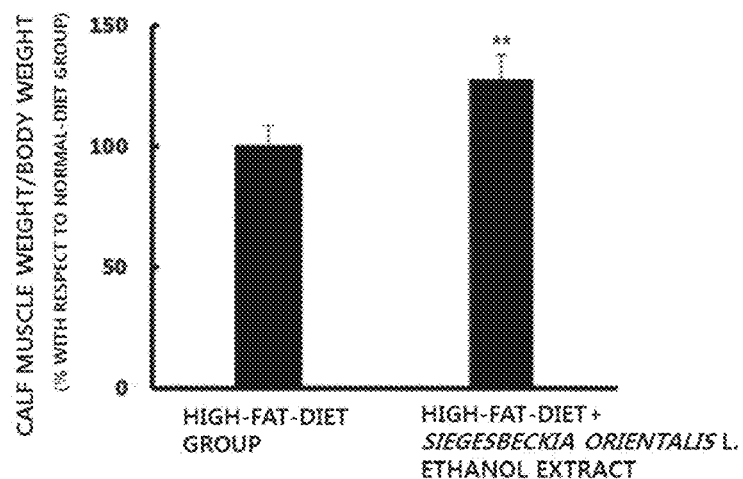
FIG. 9 shows the measurement of an increase in muscle mass in a high-fat-diet animal model after the administration of a kirenol-containing ethanol extract of *Siegesbeckia orientalis* L.

As shown in FIG. 9, the group administered the *Siegesbeckia orientalis* L. ethanol extract exhibited a 23% increase in muscle weight as compared to the control group.

Such results indicate that kirenol, a kirenol-containing *Siegesbeckia herba* extract, or a fraction of the *Siegesbeckia herba* extract according to the present invention is effective for increasing muscle mass.

EXAMPLE 8-3

Effectiveness on increasing muscle volume

Muscle volumes of the high-fat diet mice of Example 8-1 were measured in the same manner as in Example 7-3.

Figure 10:
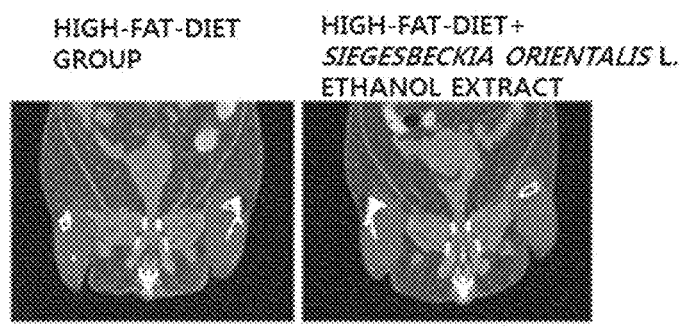
FIG. 10 shows the measurement of an increase in muscle volume in a high-fat-diet animal model after the administration of a kirenol-containing ethanol extract of *Siegesbeckia orientalis* L. (left: PET/CT result, right: muscle volume measurement result)
Figure 10:
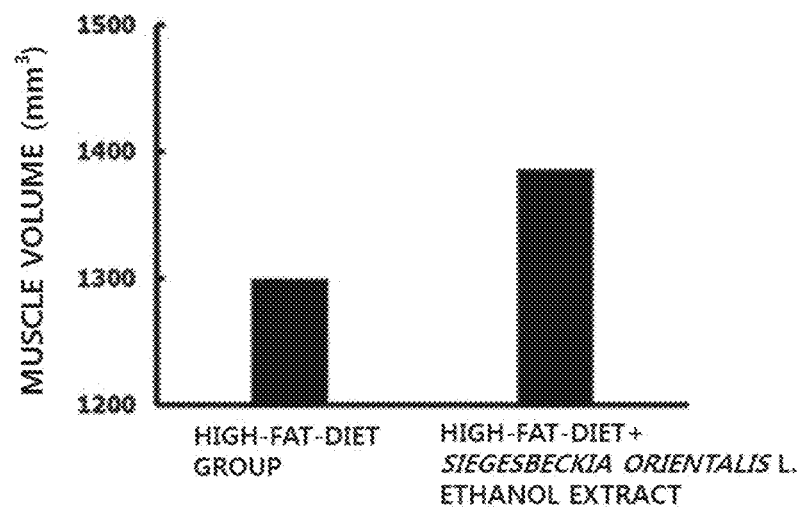

As shown in FIG. 10, the group administered the *Siegesbeckia orientalis* L. ethanol extract exhibited a 6% increase in muscle volume as compared to the control group.

Such results indicate that kirenol, a kirenol-containing *Siegesbeckia herba* extract, or a fraction of the *Siegesbeckia herba* extract according to the present invention is effective for increasing muscle mass by increasing muscle volume.

EXAMPLE 9

Effectiveness on increasing protein expression of PGC-1α, which is major gene involved in exercise ability

EXAMPLE 9-1

Effectiveness of kirenol or kirenol-containing ethanol extract of *Siegesbeckia glabrescens* Mak., *Siegesbeckia pubescens* Mak., and *Siegesbeckia orientalis* L. on increasing exercise ability L6 myoblasts (myoblast; American Type Culture Collection, Manassas, Va., USA), which are muscle cells, were incubated in DMEM (Hyclone) containing 10% fetal bovine serum (FBS; Hyclone, Logan, Utah, USA), 100 U/mL penicillin, and 100 μg/mL streptomycin (Gibco, Grand Island, N.Y., USA). The L6 cells were treated with the *Siegesbeckia glabrescens* Mak. ethanol extract prepared according to Example 1-1, *Siegesbeckia pubescens* Mak. ethanol extract prepared according to Example 2-1, or *Siegesbeckia orientalis* L. ethanol extract prepared according to Example 3-1, each at a concentration of 10 ppm. Also, L6 cells were treated with 10 μM kirenol prepared according to Example 4. In this case, a group treated with 0.01% DMSO instead of being treated with a sample was prepared as a control group. 24 hours later, the L6 cells were dissolved in a RIPA (ELPIS-Biotech, Daejeon, Korea) buffer solution containing a proteinase inhibitor cocktail (Sigma-Aldrich, St. Louis, Mo., USA). The samples were boiled for five minutes, and then an identical amount of protein (20 μg) was separated using 10% SDS-PAGE for electrophoresis. After electrophoresis, the proteins that had been separated were transferred onto a nitrocellulose membrane and western blotting was performed. The proteins were reacted with a primary antibody, and were washed three times for ten minutes using Tris-buffered saline containing 0.1% Tween 20 (TBST). In this case, the primary antibody used in the present invention was diluted at a ratio of 1:1000. A secondary antibody (anti-rabbit horseradish) was added onto the membrane that had been subjected to the primary antibody reaction, and then a secondary antibody reaction was carried out for two hours at room temperature. In this case, the secondary antibody was diluted at a ratio of 1:5000. The protein bands were colored with ECL western blotting detection reagents (Amersham, Tokyo, Japan) for the confirmation of the protein expression of PGC-1α, which is a major gene concerned with exercise ability, and α-tubulin was used to indicate that a constant amount of protein was loaded into each lane.

Figure 11:
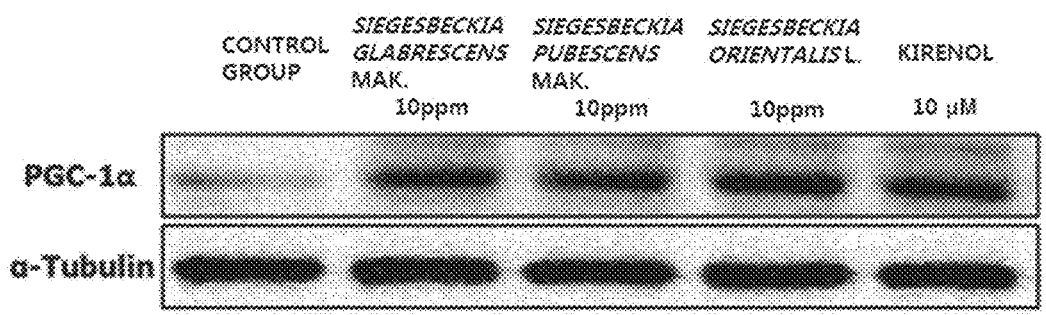
FIG. 11 shows the measurement of the protein expression levels of PGC-1α in L6 muscle cells after treatment with kirenol or a kirenol-containing ethanol extract of *Siegesbeckia glabrescens* Mak., *Siegesbeckia pubescens* Mak., or *Siegesbeckia orientalis* L.

As shown in FIG. 11, the protein expression level of PGC-1α, which is a major gene concerned with exercise ability, increased as a result of treatment with kirenol or a kirenol-containing ethanol extract of *Siegesbeckia glabrescens* Mak., *Siegesbeckia pubescens* Mak., or *Siegesbeckia orientalis* L.

Such results indicate that kirenol, a *Siegesbeckia herba* extract containing kirenol, or a fraction of the *Siegesbeckia herba* extract according to the present invention exhibits an activity of enhancing exercise ability by increasing the PGC-1α protein expression level.

EXAMPLE 9-2

Effect of ultra-high pressure extract of *Siegesbeckia orientalis* L. on exercise ability enhancement The ultra-high pressure extract of *Siegesbeckia orientalis* L. prepared according to Example 3-5 was used to treat muscle cells in the same manner as in Example 9-1. In this case, the concentration of the ultra-high pressure extract was set at 10, 20, or 40 ppm.

Figure 12:
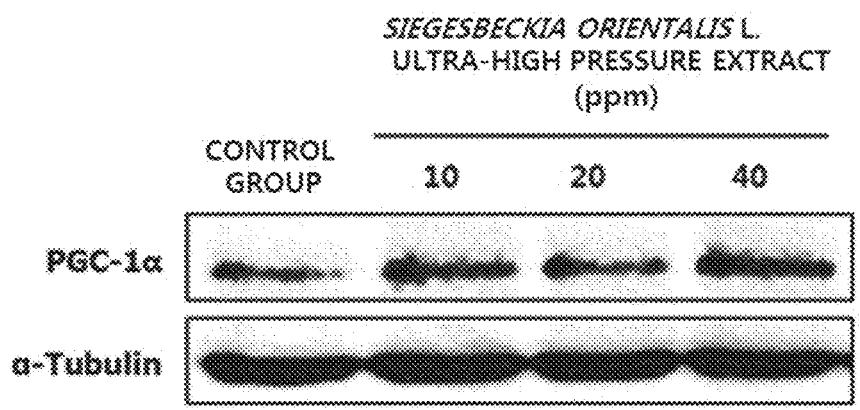
FIG. 12 shows the measurement of the protein expression levels of PGC-1α in L6 muscle cells after treatment with a kirenol-containing, ultra-high pressure extract of *Siegesbeckia orientalis* L.

As shown in FIG. 12, the protein expression level of PGC-1α, which is a major gene concerned with exercise ability, increased as a result of treatment with a kirenol-containing ultra-high pressure extract of *Siegesbeckia orientalis* L.

Such results indicate that kirenol, a *Siegesbeckia herba* extract containing kirenol, or a fraction of the *Siegesbeckia herba* extract according to the present invention exhibits an activity of enhancing exercise ability by increasing the PGC-1α protein expression level.

EXAMPLE 9-3

Effect of ethyl acetate extract of *Siegesbeckia herba* on exercise ability enhancement Each of the ethyl acetate extract of *Siegesbeckia glabrescens* Mak. prepared according to Example 1-4, the ethyl acetate extract of *Siegesbeckia pubescens* Mak. prepared according to Example 2-4, and the ethyl acetate extract of *Siegesbeckia orientalis* L. prepared according to Example 3-4 was used to treat muscle cells in the same manner as in Example 5-1. In this case, the concentrations of the ethyl acetate extracts were set at 10 ppm.

ECL western blotting detection reagents (Amersham, Tokyo, Japan) were used to color PGC-1α protein bands, and the G:BOX EF imaging system (Syngene, Cambridge, UK) was used to measure the densities of the colored protein bands. In this case, relative densities of protein bands of experimental groups treated with a sample were determined as a percentage (%), with the density of the control protein band being 100%.

The results are provided in the following Table 4:

TABLE 4

Effect of ethyl acetate extracts of *Siegesbeckia* herba on increasing PGC-1α protein expression level

| Groups | Relative density (%) |
|---|---|
| Control group | 100 |
| Example 1-4 | 132 |
| Example 2-4 | 129 |
| Example 3-4 | 137 |

As shown in Table 4, ethyl acetate extracts of *Siegesbeckia glabrescens* Mak., *Siegesbeckia pubescens* Mak., and *Siegesbeckia orientalis* L. increase the protein expression level of PGC-1α, which is a major gene concerned with exercise ability.

Such results indicate that kirenol, a *Siegesbeckia* herba extract containing kirenol, or a fraction of the *Siegesbeckia* herba extract according to the present invention exhibits an activity of enhancing exercise ability by increasing the PGC-1α protein expression level.

EXAMPLE 9-4

Effect of supercritical extracts and subcritical extracts of *Siegesbeckia* herba on exercise ability enhancement Each of the supercritical extract and subcritical extract of *Siegesbeckia glabrescens* Mak. prepared according to Examples 1-6 and 1-7, the supercritical extract and subcritical extract of *Siegesbeckia pubescens* Mak. prepared according to Examples 2-6 and 2-7, and the supercritical extract and subcritical extract of *Siegesbeckia orientalis* L. prepared according to Examples 3-6 and 3-7 was used to treat muscle cells in the same manner as in Example 5-1. In this case, the concentrations of the extracts were set at 20 ppm. Then, relative densities of protein bands of experimental groups treated with a sample were determined as a percentage (%) in the same manner as in Example 9-3, with the density of the control protein band being 100%.

The results are provided in the following Table 5:

TABLE 5

Effect of supercritical extracts and subcritical extracts of *Siegesbeckia* herba on increasing PGC-1α protein expression level

| Groups | Relative density (%) |
|---|---|
| Control group | 100 |
| Example 1-6 | 132 |
| Example 1-7 | 153 |
| Example 2-6 | 159 |
| Example 2-7 | 164 |

TABLE 5-continued

Effect of supercritical extracts and subcritical extracts of *Siegesbeckia* herba on increasing PGC-1α protein expression level

| Groups | Relative density (%) |
|---|---|
| Example 3-6 | 140 |
| Example 3-7 | 178 |

As shown in Table 5, supercritical extracts and subcritical extracts of *Siegesbeckia glabrescens* Mak., *Siegesbeckia pubescens* Mak., and *Siegesbeckia orientalis* L. increase the protein expression level of PGC-1α, which is a major gene concerned with exercise ability.

Such results indicate that kirenol, a *Siegesbeckia* herba extract containing kirenol, or a fraction of the *Siegesbeckia* herba extract according to the present invention exhibits an activity of enhancing exercise ability by increasing the PGC-1α protein expression level.

EXAMPLE 9-5

Effect of ethanol extract fraction of *Siegesbeckia orientalis* L. on exercise ability enhancement Fraction No. 6, which had been obtained by fractionating the *Siegesbeckia orientalis* L. ethanol extract of Example 4-1 using a solvent mixture of ethyl acetate and methanol mixed at 10:0.5 (v/v), was used to treat muscle cells in the same manner as in Example 5-1. In this case, the concentration of Fraction No. 6 was set at 20 ppm. Then, the relative density of protein bands of the experimental group treated with a sample was determined as a percentage (%) in the same manner as in Example 5-3, with the density of the control protein band being 100%.

The result shows that the relative density of the fraction of the *Siegesbeckia orientalis* L. ethanol extract is 168% with respect to the control group, indicating that fraction of the *Siegesbeckia orientalis* L. ethanol extract contributes to an increase in the protein expression level of PGC-1α, which is a major gene concerned with exercise ability.

Such a result indicates that kirenol, a *Siegesbeckia* herba extract containing kirenol, or a fraction of the *Siegesbeckia* herba extract according to the present invention exhibits an activity of enhancing exercise ability by increasing the PGC-1α protein expression level.

EXAMPLE 10

Confirmation of exercise ability enhancement in normal-diet animal model

EXAMPLE 10-1

Test animal diet

Four-week-old male C57BL/6 mice were adapted for one week and were provided with a normal diet (Research Diets D12450B, 10% kcal from fat, New Brunswick, N.J., USA). For the experiment, the mice were divided randomly into a total of three groups with five mice per group on the basis of body weight. Each of kirenol prepared according to Example 4 and the *Siegesbeckia orientalis* L. ethanol extract prepared according to Example 3-1 was suspended in 0.25% carboxymethyl cellulose, and the suspension was orally administered to an experimental group at a concentration of 250 mg of *Siegesbeckia orientalis* L. ethanol extract/day/kg body weight once a day at a constant time for six weeks. The control group was orally administered only the same amount of 0.25% carboxymethyl cellulose. The dietary dose and weight of the mice to which a sample was administered were measured once every week.

EXAMPLE 10-2

Effectiveness on enhancing exercise ability

After six weeks of administration, the exercise ability was evaluated using a treadmill. The assessment of exercise ability was configured to measure the maximum exercise ability of a test animal by making the animal run, at an inclination of 5°, for 20 minutes at a speed of 25 cm/s, for 20 minutes at a speed of 30 cm/s, for 20 minutes at a speed of 33 cm/s, for 20 minutes at a speed of 36 cm/s, and for 15 minutes at a speed of 36 cm/s and, at an inclination of 10°, for 15 minutes at a speed of 38 cm/s, and then at a speed of 41 cm/s until exhaustion. The maximum exercise ability was defined as a time point at which the test animal that had begun exercising failed to catch up to the treadmill speed for over ten seconds or a time point at which the cumulative number of electric shocks exceeded 100 within five minutes. The maximum exercise ability was measured in terms of the running distance and running time of the test animal. A t-test was conducted on the control group and a *Siegesbeckia orientalis* L. ethanol extract administration group to verify the statistical significance of test results, and a statistically significant difference was observed (**$p<0.01$).

As shown in FIG. 13, the exercise ability increased in the group administered a kirenol-containing *Siegesbeckia orientalis* L. ethanol extract as compared to the control group (a: running distance, b: running time).

Such results indicate that kirenol, a kirenol-containing *Siegesbeckia herba* extract, or a fraction of the *Siegesbeckia herba* extract according to the present invention is effective for enhancing exercise ability.

EXAMPLE 10-3

Effectiveness of hot-water extract of *Siegesbeckia herba* on enhancing exercise ability Running times after treatment with each of the hot-water extract of *Siegesbeckia glabrescens* Mak. prepared according to Example 1-2, hot-water extract of *Siegesbeckia pubescens* Mak. prepared according to Example 2-2, and hot-water extract of *Siegesbeckia orientalis* L. prepared according to Example 3-2 were measured in the same manner as in Examples 10-1 and 10-2.

The results are provided in the following Table 6:

TABLE 6

Effectiveness of hot-water extract of *Siegesbeckia* herba on enhancing exercise ability

| Groups | Running time (min) |
| --- | --- |
| Control group | 95 ± 3.7 |
| Example 1-2 | 111 ± 4.1** |
| Example 2-2 | 116 ± 3.6** |
| Example 3-2 | 120 ± 5.2** |

As shown in Table 6, the running time significantly increased ($p<0.01$) in groups administered the hot-water extract of *Siegesbeckia glabrescens* Mak., *Siegesbeckia pubescens* Mak., or *Siegesbeckia orientalis* L. as compared to the control group.

Such results indicate that kirenol, a kirenol-containing *Siegesbeckia herba* extract, or a fraction of the *Siegesbeckia herba* extract according to the present invention is effective for enhancing exercise ability.

EXAMPLE 11

Confirmation of exercise ability enhancement in obese animal model induced by high-fat diet

EXAMPLE 11-1

Test animal diet

Four-week-old male C57BL/6 mice were adapted for one week and were provided with a high-fat diet (Research Diets D12492, 60% kcal from fat) for six weeks to induce obesity. The mice were divided randomly into a total of two groups with five mice per group, and were subjected to oral administration in the same manner as in Example 10-1.

EXAMPLE 11-2

Effectiveness on enhancing exercise ability

The exercise ability of a high-fat-diet induced obese animal model was assessed in the same manner as in Example 10-2. A t-test was conducted on the high-fat diet control group and the high-fat diet group administered a *Siegesbeckia orientalis* L. ethanol extract to verify the statistical significance of test results, and a statistically significant difference was observed (**$p<0.01$).

As shown in FIG. 14, the exercise ability increased in the high-fat diet group administered a *Siegesbeckia orientalis* L. ethanol extract as compared to the high-fat diet control group (a: running distance, b: running time).

Such results indicate that kirenol, a kirenol-containing *Siegesbeckia herba* extract, or a fraction of the *Siegesbeckia herba* extract according to the present invention is effective for enhancing exercise ability in an obese model.

EXAMPLE 12

Effectiveness on enhancing protein expression of gene related to exercise ability enhancement in muscle tissue of animal models Calf muscle was extracted from a normal diet mouse of Example 10-1 and a high-fat diet mouse of Example 11-1. Western blotting was performed to evaluate the protein expression of p-AMPK, SIRT1, PGC-1α, and PPARδ, and α-tubulin was used to indicate that a constant amount of protein was loaded into each lane.

Figure 15:
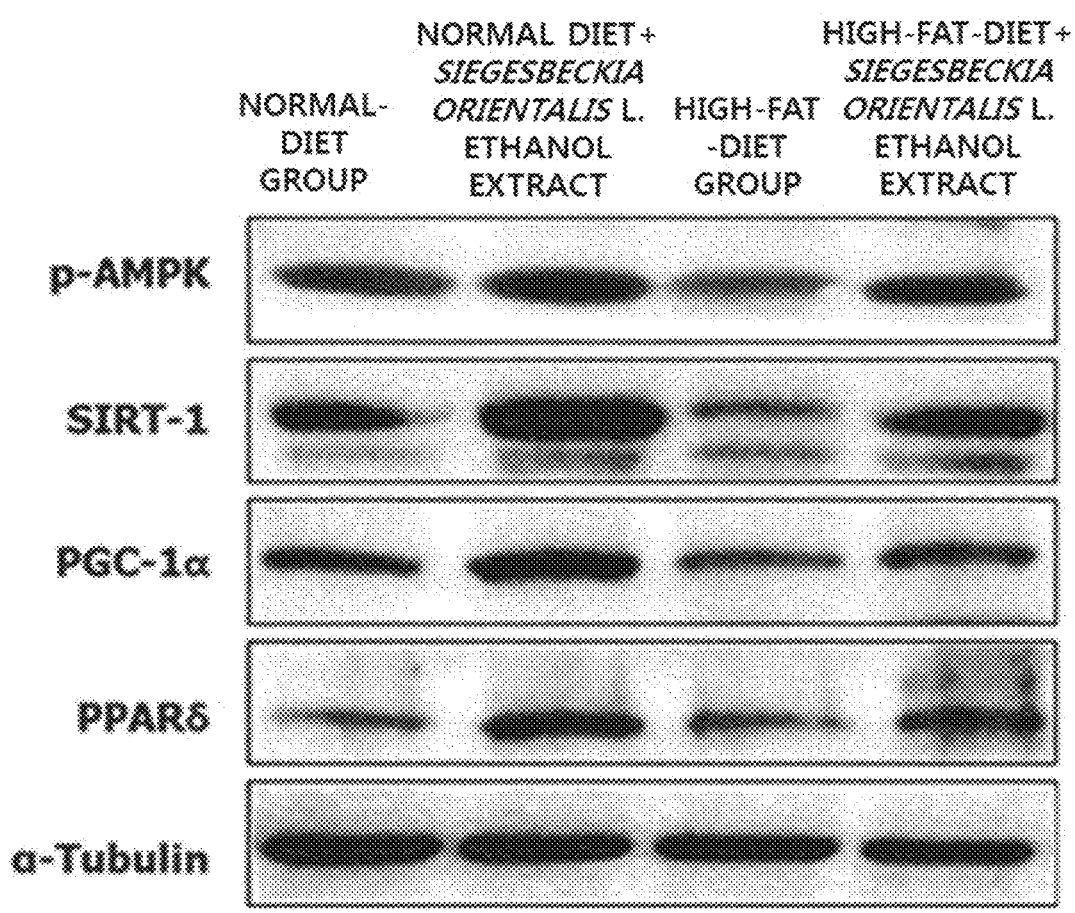
FIG. 15 shows the measurement of the protein expression levels of p-AMPK, SIRT1, PGC-1α, and PPARδ, which are genes associated with exercise ability improvement, in calf muscle of an animal model after the administration of a kirenol-containing ethanol extract of *Siegesbeckia orientalis* L.

As shown in FIG. 15, a *Siegesbeckia orientalis* L. extract increased protein expression levels of p-AMPK, SIRT1, PGC-1α, and PPARδ, all of which are genes concerned with exercise ability enhancement, in the normal-diet model and the high-fat-diet model.

Such results indicate that kirenol, a *Siegesbeckia herba* extract containing kirenol, or a fraction of the *Siegesbeckia herba* extract according to the present invention is effective for enhancing exercise ability in animal models by increasing the protein expression of genes related to exercise ability enhancement.

EXAMPLE 13

Effectiveness on enhancing protein expression of gene related to mitochondrial biosynthesis in muscle tissue of animal models Calf muscle was extracted from a normal diet mouse of Example 10-1 and a high-fat diet mouse of Example 11-1. RT-PCR was performed to evaluate the mRNA expression of PGC-1α, NRF-1, ERRα, and Tfam. TRIzol Reagent (Invitrogen, Carlsbad, Calif., USA) was used for harvesting total RNA from the calf muscle, and the total RNA was reverse transcribed. The RT-PCR analysis was carried out as follows: First, the RNA was reverse transcribed for cDNA synthesis by using a reverse transcriptase. RT-PCR was conducted using specific primers as listed below:

```
PGC-1α:
(Forward primer)
SEQ ID NO: 11:
5'-ATGTGTCGCCTTCTTGCTCT-3'

(Reverse primer)
SEQ ID NO: 12:
5'-ATCTACTGCCTGGGGACCTT-3'

ERRα:
(Forward primer)
SEQ ID NO: 13:
5'-GCTGGTGGTTGAACCTGAGA-3'

(Reverse primer)
SEQ ID NO: 14:
5'-GGGCTAACACCCTATGCCAG-3'

NRF-1:
(Forward primer)
SEQ ID NO: 15:
5'-TGGACCCAAGCATTACGGAC-3'

(Reverse primer)
SEQ ID NO: 16:
5'-GGTCATTTCACCGCCCTGTA-3'

Tfam:
(Forward primer)
SEQ ID NO: 17:
5'-TCGCCTGTCAGCCTTATCTG-3'

(Reverse primer)
SEQ ID NO: 18:
5'-CCGGGCTTCCTTCTCTAAC-3'

β-actin:
(Forward primer)
SEQ ID NO: 19:
5'-TAACCAACTGGGACGATATG-3'

(Reverse primer)
SEQ ID NO: 20:
5'-ATACAGGGACAGCACAGCCT-3'
```

Figure 16:
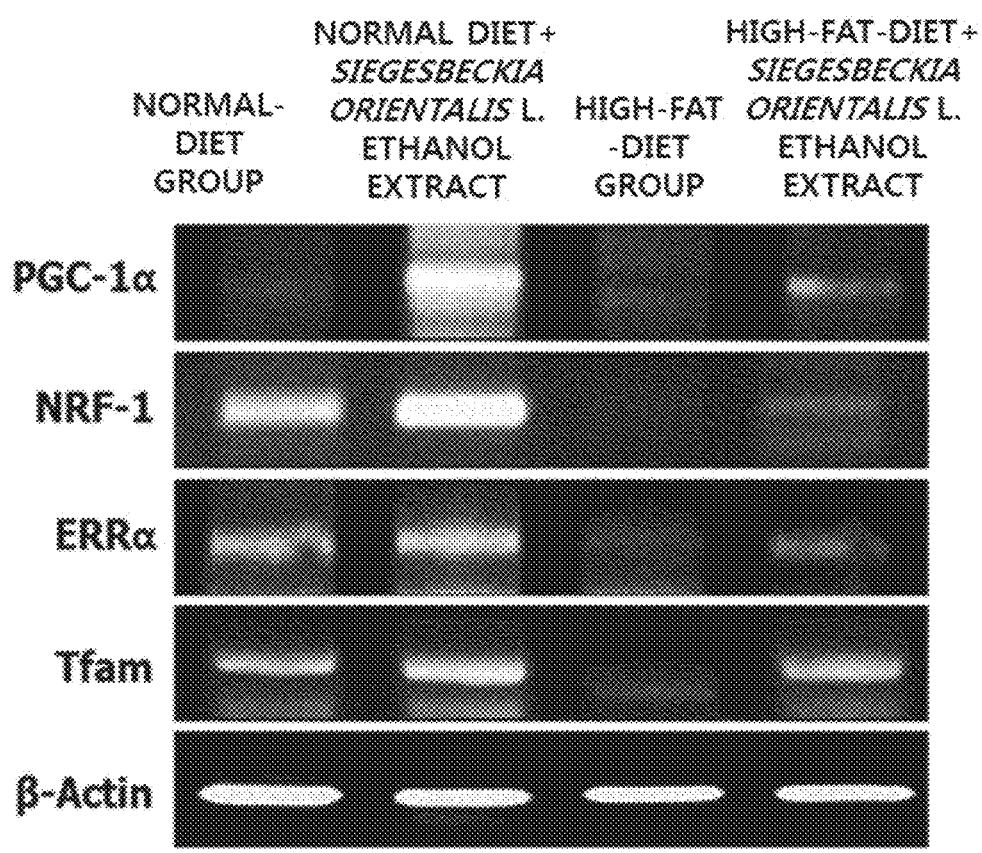
FIG. 16 shows the measurement of mRNA expression levels of PGC-1α, NRF-1, ERRα, and Tfam, which are genes associated with mitochondrial biosynthesis, in calf muscle of an animal model after the administration of a kirenol-containing ethanol extract of *Siegesbeckia orientalis* L.

As shown in FIG. 16, a *Siegesbeckia orientalis* L. extract increases mRNA expression levels of PGC-1α, NRF-1, ERRα, and Tfam, which are genes concerned with mitochondrial biosynthesis, in the normal-diet model and the high-fat-diet model.

Such results indicate that kirenol, a *Siegesbeckia herba* extract containing kirenol, or a fraction of the *Siegesbeckia herba* extract according to the present invention is effective for enhancing exercise ability by increasing mitochondrial biosynthesis.

Hereinafter, preparation examples of food or pharmaceutical products including kirenol or a kirenol-containing *Siegesbeckia herba* extract as an active ingredient for muscle function improvement or exercise ability enhancement will be described. However, those preparation examples are not to limit the present invention thereto but are intended only to describe the present invention in detail. The food composition of Preparation Example 1 and pharmaceutical composition of Preparation Example 2 for muscle function improvement or exercise ability enhancement were prepared based on kirenol, which exhibits an excellent muscle function improvement or exercise ability enhancement efficacy, or a kirenol-containing *Siegesbeckia herba* extract by using a common method and according to the composition and composition ratio as listed below.

PREPARATION EXAMPLE 1

Foods

PREPARATION EXAMPLE 1-1

Health foods

The health food may be prepared by mixing 1000 mg of the *Siegesbeckia herba* extract of Examples 1 to 3 or kirenol, 70 μg vitamin A acetate, 1.0 mg vitamin E, 0.13 mg vitamin B1, 0.15 mg vitamin B2, 0.5 mg vitamin B6, 0.2 μg vitamin B12, 10 mg vitamin C, 10 μg biotin, 1.7 mg nicotinic acid amide, 50 μg folic acid, 0.5 mg calcium pantothenate, 1.75 mg ferrous sulfate, 0.82 mg zinc oxide, 25.3 mg magnesium carbonate, 15 mg potassium phosphate monobasic, 55 mg dicalcium phosphate, 90 mg potassium citrate, 100 mg calcium carbonate, and 24.8 mg magnesium chloride. The mixing ratio may be arbitrarily modified. The above ingredients may be mixed according to a common method of preparing health food, and the mixture may be formed into granules and be used for preparing a health food composition according to a common method.

PREPARATION EXAMPLE 1-2

Health drinks 1000 mg of the *Siegesbeckia herba* extract of Examples 1 to 3 or kirenol, 1000 mg citric acid, 100 g oligosaccharide, 2 g plum concentrate, and 1 g taurine are mixed, and purified water was added to the mixed ingredients until 900 ml of the mixture ingredient and purified water. The above mixture are mixed according to a common method of preparing a health drink, and the mixture is heated at 85° C. for about one hour while stirring. The prepared solution is filtered and collected in a sterilized 2 L container, the container is sealed, and the content is sterilized. After refrigeration, the substances may be used for preparing a health drink composition.

PREPARATION EXAMPLE 1-3

Chewing gum

Chewing gum was prepared based on a mixture consisting of 20 wt % gum base, 76.9 wt % sugar, 1 wt % flavoring agent, 2 wt % water, and 0.1 wt % of the *Siegesbeckia herba* extract of Examples 1 to 3 or kirenol, and the preparation was carried out according to a common method.

PREPARATION EXAMPLE 1-4

Candies

Candies were prepared based on a mixture consisting of 60 wt % sugar, 39.8 wt % starch syrup, 0.1 wt % flavoring agent, and 0.1 wt % of the *Siegesbeckia herba* extract of Examples 1 to 3 or kirenol, and the preparation was carried out according to a common method.

PREPARATION EXAMPLE 1-5

Biscuits

Biscuits were prepared based on a mixture consisting of 25.59 wt % first-class weak flour, 22.22 wt % first-class medium flour, 4.80 wt % refined sugar, 0.73 wt % table salt, 0.78 wt % glucose, 11.78 wt % palm shortening, 1.54 wt % ammonium, 0.17 wt % baking soda, 0.16 wt % sodium bisulfite, 1.45 wt % rice flour, 0.0001 wt % vitamin B, 0.04 wt % milk flavor, 20.6998 wt % water, 1.16 wt % whole milk powder, 0.29 wt % replacement milk, 0.03 wt % calcium phosphate monobasic, 0.29 wt % salt spray, 7.27 wt % oil spray, and 1.0001 wt % of the *Siegesbeckia herba* extract of Examples 1 to 3 or kirenol, and the preparation was carried out according to a common method.

PREPARATION EXAMPLE 2

Pharmaceutical products

PREPARATION EXAMPLE 2-1

Powders

A powder was prepared by mixing 50 mg of the *Siegesbeckia herba* extract of Examples 1 to 3 or kirenol with 2 g crystalline cellulose, and charging the mixture charged into an airtight package according to a common powder preparation method.

PREPARATION EXAMPLE 2-2

Tablets

Tablets were prepared by mixing 50 mg of the *Siegesbeckia herba* extract of Examples 1 to 3 or kirenol with 400 mg crystalline cellulose and 5 mg magnesium stearate, and forming the mixture into tablets by compression according to a common tablet preparation method.

PREPARATION EXAMPLE 2-3

Capsules

Capsules were prepared by mixing 30 mg of the *Siegesbeckia herba* extract of Examples 1 to 3 or kirenol with 100 mg whey protein, 400 mg crystalline cellulose, and 6 mg magnesium stearate, and charging the mixture into gelatin capsules according to a common capsule preparation method.

PREPARATION EXAMPLE 2-4

Injections

An injection was prepared according to a common injection preparation method by dissolving active ingredients in distilled water for injection, adjusting the pH to about 7.5, mixing 100 mg of kirenol of Example 3-5 with distilled water for injection and a pH adjusting agent, charging the mixture into a 2 ml ampoule, and performing sterilization thereof.

---

What is claimed is:

1. A method of improving muscular endurance in a subject, the method comprising administering to a subject an effective amount of a composition that includes a *Siegesbeckia herba* extract or a fraction of the *Siegesbeckia herba* extract as an active ingredient.

2. The method of claim 1, wherein the *Siegesbeckia herba* extract is an extract obtained from one or more selected from the group consisting of *Siegesbeckia glabrescens* Mak., *Siegesbeckia pubescens* Mak., and *Siegesbeckia orienkilis* L.

3. The method of claim 1, wherein the *Siegesbeckia herba* extract is obtained by extracting *Siegesbeckia herba* using one or more solvents selected from the group consisting of water, organic solvents having one to six carbon atoms, subcritical fluids, and supercritical fluids.

4. The method of claim 3, wherein the organic solvent having one to six carbon atoms is one or more selected from the group consisting of alcohols, acetone, ethers, benzene, chloroform, ethyl acetate, methylene chloride, hexane, cyclohexane, and petroleum ethers, all of which have one to six carbon atoms.

5. The method of claim 1, wherein the *Siegesbeckia herba* extract is obtained by extracting *Siegesbeckia herba* under ultra-high pressure conditions of 100 MPa or more.

6. The method of claim 1, wherein the fraction of the *Siegesbeckia herba* extract is obtained by fractionating the *Siegesbeckia herba* extract using ethyl acetate, methanol, or a solvent mixture of ethyl acetate and methanol.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: myogenin forward primer

<400> SEQUENCE: 1
tgggctgcca caagccagac                                              20

<210> SEQ ID NO 2
<211> LENGTH: 20
<212> TYPE: DNA
<213> ORGANISM: Artificial
<220> FEATURE:
<223> OTHER INFORMATION: myogenin reverse primer

<400> SEQUENCE: 2
cagcccagcc actggcatca                                              20

<210> SEQ ID NO 3
<211> LENGTH: 20
<212> TYPE: DNA
<213> ORGANISM: Artificial
<220> FEATURE:
<223> OTHER INFORMATION: MyoD forward primer
```

<400> SEQUENCE: 3
ggatggtgcc cctgggtcct                                           20

<210> SEQ ID NO 4
<211> LENGTH: 20
<212> TYPE: DNA
<213> ORGANISM: Artificial
<220> FEATURE:
<223> OTHER INFORMATION: MyoD reverse primer

<400> SEQUENCE: 4
tggccttcgc tgtgagtcgc                                           20

<210> SEQ ID NO 5
<211> LENGTH: 20
<212> TYPE: DNA
<213> ORGANISM: Artificial
<220> FEATURE:
<223> OTHER INFORMATION: beta actin forward primer

<400> SEQUENCE: 5
agccatgtac gtagccatcc                                           20

<210> SEQ ID NO 6
<211> LENGTH: 20
<212> TYPE: DNA
<213> ORGANISM: Artificial
<220> FEATURE:
<223> OTHER INFORMATION: beta actin reverse primer

<400> SEQUENCE: 6
ctctcagctg tggtggtgaa                                           20

<210> SEQ ID NO 7
<211> LENGTH: 20
<212> TYPE: DNA
<213> ORGANISM: Artificial
<220> FEATURE:
<223> OTHER INFORMATION: atrogin-1 forward primer

<400> SEQUENCE: 7
ccctgagtgg catcgcccaa                                           20

<210> SEQ ID NO 8
<211> LENGTH: 19
<212> TYPE: DNA
<213> ORGANISM: Artificial
<220> FEATURE:
<223> OTHER INFORMATION: atrogin-1 reverse primer

<400> SEQUENCE: 8
aggtcccgcc catcgctca                                            19

<210> SEQ ID NO 9
<211> LENGTH: 20
<212> TYPE: DNA
<213> ORGANISM: Artificial
<220> FEATURE:
<223> OTHER INFORMATION: MuRF1 forward primer

<400> SEQUENCE: 9
tctactcggc cacaggcgct                                           20

<210> SEQ ID NO 10

-continued

<210> SEQ ID NO 10
<211> LENGTH: 20
<212> TYPE: DNA
<213> ORGANISM: Artificial
<220> FEATURE:
<223> OTHER INFORMATION: MuRF1 reverse primer

<400> SEQUENCE: 10
cttgacagct cccgccgcaa                                               20

<210> SEQ ID NO 11
<211> LENGTH: 20
<212> TYPE: DNA
<213> ORGANISM: Artificial
<220> FEATURE:
<223> OTHER INFORMATION: PGC-1 alpha forward primer

<400> SEQUENCE: 11
atgtgtcgcc ttcttgctct                                               20

<210> SEQ ID NO 12
<211> LENGTH: 20
<212> TYPE: DNA
<213> ORGANISM: Artificial
<220> FEATURE:
<223> OTHER INFORMATION: PGC-1 alpha reverse primer

<400> SEQUENCE: 12
atctactgcc tggggacctt                                               20

<210> SEQ ID NO 13
<211> LENGTH: 20
<212> TYPE: DNA
<213> ORGANISM: Artificial
<220> FEATURE:
<223> OTHER INFORMATION: ERR alpha forward primer

<400> SEQUENCE: 13
gctggtggtt gaacctgaga                                               20

<210> SEQ ID NO 14
<211> LENGTH: 20
<212> TYPE: DNA
<213> ORGANISM: Artificial
<220> FEATURE:
<223> OTHER INFORMATION: ERR alpha reverse primer

<400> SEQUENCE: 14
gggctaacac cctatgccag                                               20

<210> SEQ ID NO 15
<211> LENGTH: 20
<212> TYPE: DNA
<213> ORGANISM: Artificial
<220> FEATURE:
<223> OTHER INFORMATION: NRF-1 forward primer

<400> SEQUENCE: 15
tggacccaag cattacggac                                               20

<210> SEQ ID NO 16
<211> LENGTH: 20
<212> TYPE: DNA
<213> ORGANISM: Artificial
<220> FEATURE:
<223> OTHER INFORMATION: NRF-1 reverse primer

<400> SEQUENCE: 16

```
ggtcatttca ccgccctgta                                          20

<210> SEQ ID NO 17
<211> LENGTH: 20
<212> TYPE: DNA
<213> ORGANISM: Artificial
<220> FEATURE:
<223> OTHER INFORMATION: Tfam forward primer

<400> SEQUENCE: 17
tcgcctgtca gccttatctg                                          20

<210> SEQ ID NO 18
<211> LENGTH: 19
<212> TYPE: DNA
<213> ORGANISM: Artificial
<220> FEATURE:
<223> OTHER INFORMATION: Tfam reverse primer

<400> SEQUENCE: 18
ccgggcttcc ttctctaac                                           19

<210> SEQ ID NO 19
<211> LENGTH: 20
<212> TYPE: DNA
<213> ORGANISM: Artificial
<220> FEATURE:
<223> OTHER INFORMATION: beta-actin forward primer

<400> SEQUENCE: 19
taaccaactg ggacgatatg                                          20

<210> SEQ ID NO 20
<211> LENGTH: 20
<212> TYPE: DNA
<213> ORGANISM: Artificial
<220> FEATURE:
<223> OTHER INFORMATION: beta-actin reverse primer

<400> SEQUENCE: 20
atacagggac agcacagcct                                          20
```